(12) United States Patent
Iwata

(10) Patent No.: US 8,808,341 B2
(45) Date of Patent: Aug. 19, 2014

(54) RESPIRATORY INDUCTION APPARATUS, RESPIRATORY INDUCTION PROGRAM, AND PARTICLE BEAM THERAPY SYSTEM

(75) Inventor: Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 182 days.

(21) Appl. No.: 13/140,886

(22) PCT Filed: Nov. 16, 2010

(86) PCT No.: PCT/JP2010/070362
§ 371 (c)(1),
(2), (4) Date: Jun. 20, 2011

(87) PCT Pub. No.: WO2007/014106
PCT Pub. Date: Feb. 1, 2007

(65) Prior Publication Data
US 2012/0119115 A1 May 17, 2012

(51) Int. Cl.
*A61N 1/39* (2006.01)
*A61N 5/10* (2006.01)
*A61B 5/08* (2006.01)
*G21K 5/00* (2006.01)
*A61B 6/00* (2006.01)

(52) U.S. Cl.
CPC ............. *A61B 5/08* (2013.01); *A61N 5/1048* (2013.01); *A61B 6/541* (2013.01); *A61N 5/1068* (2013.01); *G21K 5/00* (2013.01); *A61N 2005/1087* (2013.01)
USPC ........................................................ 607/1

(58) Field of Classification Search
None
See application file for complete search history.

(56) References Cited

U.S. PATENT DOCUMENTS

| 7,525,104 B2 | 4/2009 | Harada |
| 2002/0120207 A1 | 8/2002 | Hoffman |

(Continued)

FOREIGN PATENT DOCUMENTS

| JP | 2001-346773 A | 12/2001 |
| JP | 2003-33443 A | 2/2003 |

(Continued)

OTHER PUBLICATIONS

International Search Report (PCT/ISA/210) issued on Jan. 11, 2011, by Japanese Patent Office as the International Searching Authority for International Application No. PCT/JP2010/070362.

(Continued)

*Primary Examiner* — Christopher D Koharski
*Assistant Examiner* — Elizabeth K So
(74) *Attorney, Agent, or Firm* — Buchanan Ingersoll & Rooney

(57) ABSTRACT

The objective is to obtain a respiratory induction apparatus and a particle beam therapy system in which respiration can appropriately be induced by accurately evaluating the respiration. There are provided a respiratory induction control unit (7cC) that generates a desired respiratory signal ($R_{tj}(t)$) for respiratory induction; a real respiration measurement unit (7a) that outputs a real respiratory signal ($R_{rl}(t)$) obtained by measuring real respiration of a patient; and a respiration evaluation unit (7cE) in which by, as a unit, utilizing data of a single period ($T_{res}$) of the desired respiratory signal ($R_{tj}(t)$), there is calculated a pair of coefficients ($a_1$ and $b_1$), of trigonometric functions, which correspond to the 1st-order terms by means of Fourier series expansion of data of the desired respiratory signal ($R_{tj}(t)$) and data of the real respiratory signal ($R_{rl}(t)$), which is acquired in synchronization with the data of the desired respiratory signal ($R_{tj}(t)$), and there are performed comparisons between the respective gains ($G_{tj}$ and $G_{rl}$) and between the respective phases ($\phi_{tj}$ and $\phi_{rl}$), which are obtained from the coefficients ($a_1$ and $b_1$), so that there is evaluated a misalignment of the real respiration from the desired respiratory signal.

20 Claims, 10 Drawing Sheets

(56) References Cited

U.S. PATENT DOCUMENTS

| | | |
|---|---|---|
| 2006/0231775 A1 | 10/2006 | Harada |
| 2007/0076846 A1 | 4/2007 | Ruchala et al. |
| 2008/0089463 A1 | 4/2008 | Nakamura et al. |
| 2010/0207042 A1 | 8/2010 | Harada et al. |
| 2012/0211667 A1* | 8/2012 | Iwata et al. ............ 250/396 ML |

FOREIGN PATENT DOCUMENTS

| | | |
|---|---|---|
| JP | 2003-033443 A | 2/2003 |
| JP | 2006-288875 A | 10/2006 |
| JP | 2008-119449 A | 5/2008 |
| JP | 2008-259604 A | 10/2008 |
| JP | 2010-63725 A | 3/2010 |
| TW | 200730211 A | 8/2007 |
| WO | WO 2006/082651 A1 | 8/2006 |
| WO | 2007014106 A2 | 2/2007 |
| WO | WO 2009/150708 A1 | 12/2009 |

OTHER PUBLICATIONS

Office Action from Taiwanese Patent Office date Jun. 26, 2013, issued in corresponding Taiwanese Patent Application No. 100119937, with Japanese and English translation thereof. (27 pages).

Office Action from the Japan Patent Office dated Dec. 10, 2013, issued in corresponding Japanese Patent Application No. 2012-544029, with English translation thereof. (5 pages).

Extended Search Report from European Patent Office dated Mar. 4, 2014, issued in European Patent Application No. 10859863.2. (6 pages).

* cited by examiner

RESPIRATORY INDUCTION APPARATUS, RESPIRATORY INDUCTION PROGRAM, AND PARTICLE BEAM THERAPY SYSTEM

TECHNICAL FIELD

The present invention relates to a particle beam therapy system, which is a medical system that performs therapy by irradiating a charged particle beam, including a heavy ion particle beam such as a carbon ion beam or a proton beam, onto the diseased site of a cancer or the like; the present invention relates particularly to a respiratory induction apparatus that induces the respiration of a patient.

BACKGROUND ART

In the particle beam therapy, therapy is implemented by irradiating a charged particle beam (referred to as a particle beam, hereinafter) onto a diseased site, which is a therapy subject, so as to cause damage to diseased tissue; it is required to give a sufficient dose to the diseased tissue, which is an irradiation subject, and suppress a dose to the peripheral tissues. Accordingly, there is generated a treatment plan in order to control the irradiation dose and the irradiation coverage (referred to as an irradiation field, hereinafter) in accordance with the preliminarily measured shape of the irradiation subject. However, a treatment plan is generated under the assumption that neither the shape of an irradiation subject changes nor the position thereof is displaced; therefore, in the case where the irradiation subject is displaced due to respiration, the planned irradiation cannot be performed. Thus, with regard to an irradiation subject whose position is displaced due to respiration, there has been proposed a particle beam therapy system in which a respiratory phase is measured, and then a particle beam is irradiated onto the irradiation subject at the respiratory phase when the position and the shape are stabilized, i.e., beam irradiation is controlled through respiration synchronization (for example, refer to Patent Documents 1 and 2).

Furthermore, by focusing attention on the fact that respiration can be controlled consciously, there has been proposed a particle beam therapy system having a respiratory induction function in which the timing of expiration or inspiration is indicated so as to induce the respiration of a patient into the respiration of a predetermined period (for example, Patent Documents 3 through 6).

PRIOR ART REFERENCE

Patent Document

[Patent Document 1] Japanese Patent Application Laid-Open No. 2006-288875 (Paragraphs 0037 through 0040, FIGS. 7 through 9)
[Patent Document 2] International Publication No. WO2006/082651A1 (Paragraphs 0092 through 0096, FIG. 16)
[Patent Document 3] Japanese Patent Application Laid-Open No. 2001-346773 (paragraphs 0013 through 0015, FIG. 1)
[Patent Document 4] Japanese Patent Application Laid-Open No. 2008-119449 (Paragraphs 0014 through 0020, FIGS. 4 and 5)
[Patent Document 5] Japanese Patent Application Laid-Open No. 2008-259604 (Paragraphs 0058 through 0059, FIG. 3)
[Patent Document 6] International Publication No. WO2009/150708A1 (Paragraphs 0021 through 0026, FIGS. 1 and 6)

DISCLOSURE OF THE INVENTION

Problem(s) to be Solved by the Invention

Such a respiratory induction function as described above induces the respiration of a patient into the respiration of a period that is suited to the operation cycle of an accelerator or the like so that beam irradiation can efficiently be performed; it is described therein that in the case where the timing of real respiration is different from an indicated timing, there is given an instruction for modifying the pace or depth of the respiration. However, in any particle beam therapy system, when respiration is evaluated, there is evaluated the position of the vertex or the base (maximum value/minimum value) of a respiratory waveform, which is the temporal change of a respiratory signal, or the position or the length of the portion, of the respiratory waveform, that is above a threshold value (or below the threshold value); other portions are not evaluated. Therefore, for example, in the case where respiration is irregular or in the case where noise is superimposed on the respiratory waveform, i.e., in the case where an unanticipated waveform is caused, the respiration cannot accurately be evaluated and hence no appropriate control or instruction can be implemented. In other words, irradiation cannot be implemented at an optimum timing for the respiration.

The present invention has been implemented in order to solve the foregoing problems; the objective thereof is to obtain a respiratory induction apparatus and a particle beam therapy system in which respiration can appropriately be induced by accurately evaluating the respiration.

Means for Solving the Problems

A respiratory induction apparatus according to the present invention induces respiration of a patient in particle beam therapy and is characterized by including a desired respiratory signal generating unit that generates a desired respiratory signal for inducing respiration of the patient; a real respiration measurement unit that measures real respiration of the patient and outputs a real respiratory signal obtained through the measurement; and a respiration evaluation unit in which by, as a calculation unit, utilizing data of a single period of the desired respiratory signal, there is calculated a pair of coefficients, of trigonometric functions, which correspond to the 1st-order terms by means of Fourier series expansion of data of the desired respiratory signal and data of the real respiratory signal, which is acquired in synchronization with the data of the desired respiratory signal, and there are performed comparisons between the respective gains and between the respective phases, which are obtained from the calculated coefficients, so that there is evaluated a misalignment of the real respiration from the desired respiratory signal.

A respiratory induction program according to the present invention establishes on a computer a respiratory induction apparatus that induces respiration of a patient in particle beam therapy, and is characterized by including a desired respiratory signal generating step in which there is generated a desired respiratory signal for inducing respiration of the patient; a real respiration measurement step in which real respiration of the patient is measured and a real respiratory signal obtained through the measurement is outputted; and a respiration evaluation step in which by, as a calculation unit, utilizing data of a single period of the desired respiratory signal, there is calculated a pair of coefficients, of trigonometric functions, which correspond to the 1st-order terms by means of Fourier series expansion of data of the desired respiratory signal and data of the real respiratory signal, which is acquired in synchronization with the data of the desired respiratory signal, and there are performed comparisons between the respective gains and between the respective phases, which are obtained from the calculated coefficients, so that there is evaluated a misalignment of the real respiration from the desired respiratory signal.

A particle beam therapy system according to the present invention is characterized by including an accelerator that generates a particle beam; a plurality of treatment rooms; a particle beam transport path that connects the accelerator with each of the plurality of treatment rooms; a switching device, provided in the transport path, that switches the orbits of a particle beam generated by the accelerator, in such a way that the particle beam is supplied to one of the plurality of treatment rooms; the respiratory induction apparatus provided in each of the plurality of treatment rooms; and an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

Advantage of the Invention

In a respiratory induction apparatus and a particle beam therapy system according to the present invention, respiration is evaluated based on the gain and the phase calculated by use of a pair of coefficients, of trigonometric functions, corresponding to 1st-order terms by means of Fourier series expansion of respective signal data pieces acquired with the period of the desired respiratory signal, which is a definite periodic function, from the real respiratory signal and the desired respiratory signal; therefore, the objective is to obtain a respiratory induction apparatus and a particle beam therapy system in which respiration can appropriately be induced by accurately evaluating the respiration.

BEST MODE FOR CARRYING OUT THE INVENTION

Embodiment 1

Figure 1:
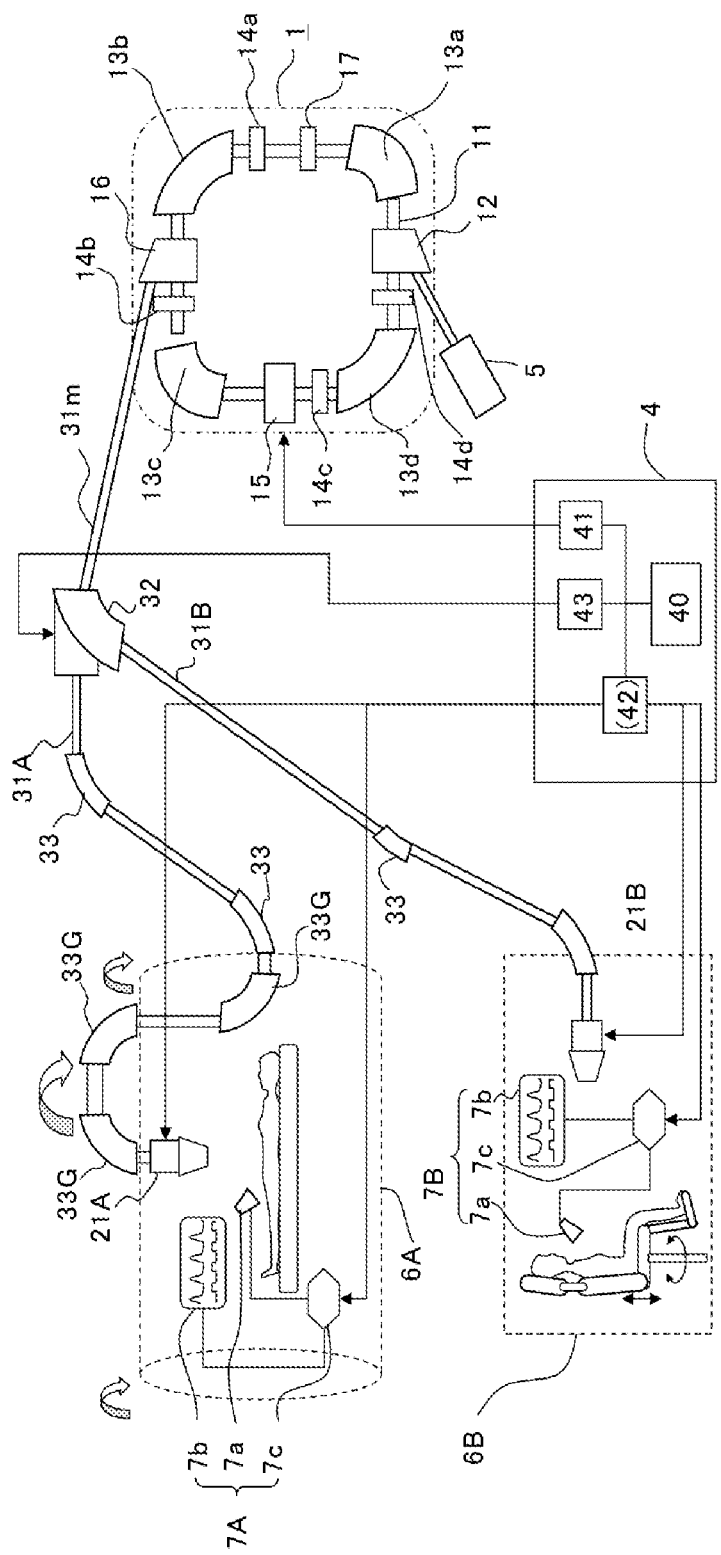
FIG. 1 is a diagram for explaining the overall configuration of a particle beam therapy system provided with a respiratory induction apparatus according to Embodiment 1 of the present invention.
Figure 2:
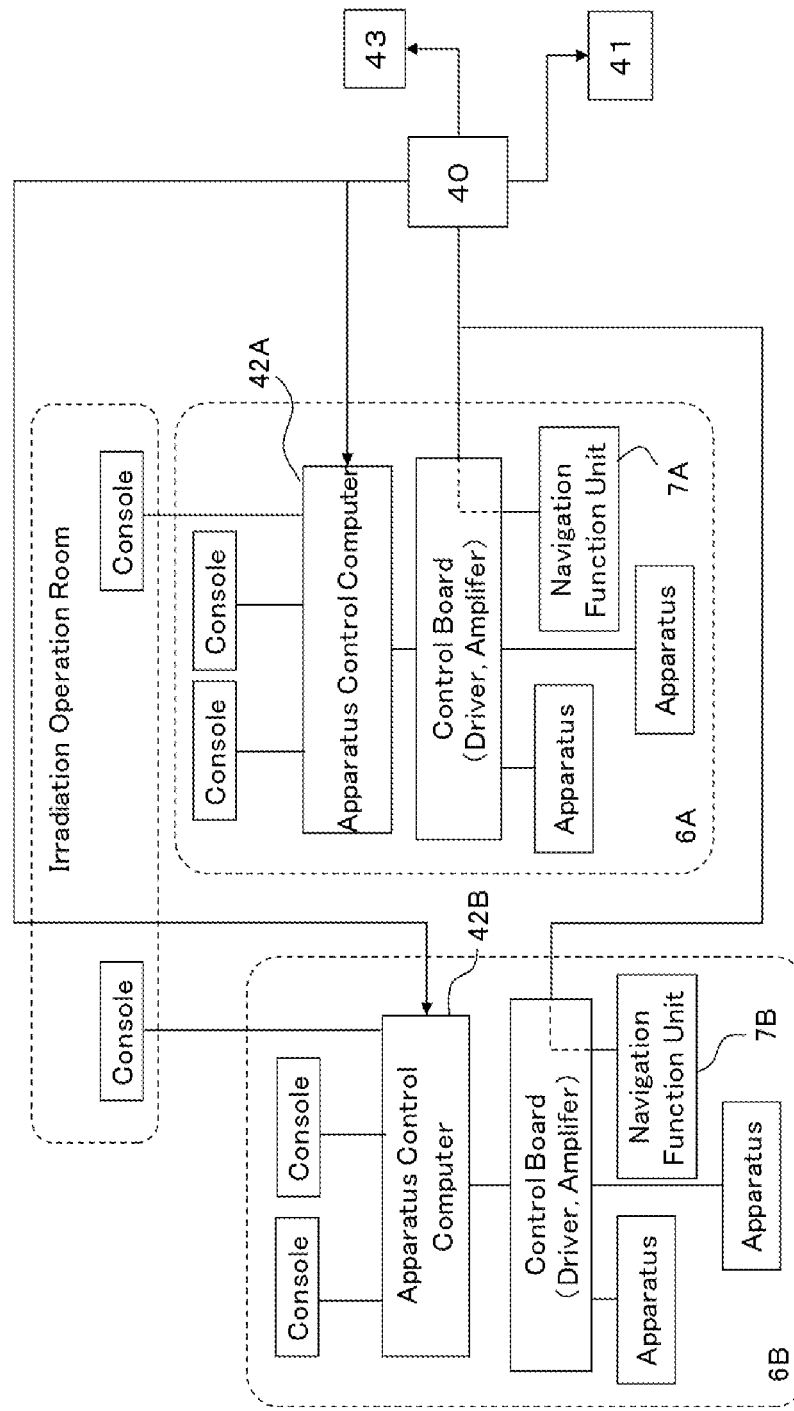
FIG. 2 is a functional block diagram for explaining the configuration of the control system in a particle beam therapy system provided with a respiratory induction apparatus according to Embodiment 1 of the present invention.
Figure 3:
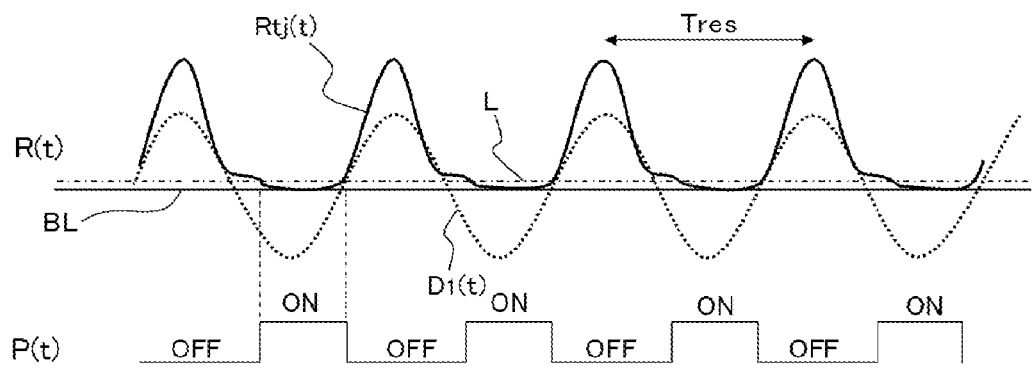
FIG. 3 is a waveform chart representing the relationship among a desired respiratory signal, an evaluation function, and a respiration gate signal utilized in a respiratory induction apparatus according to Embodiment 1 of the present invention.
Figure 4:
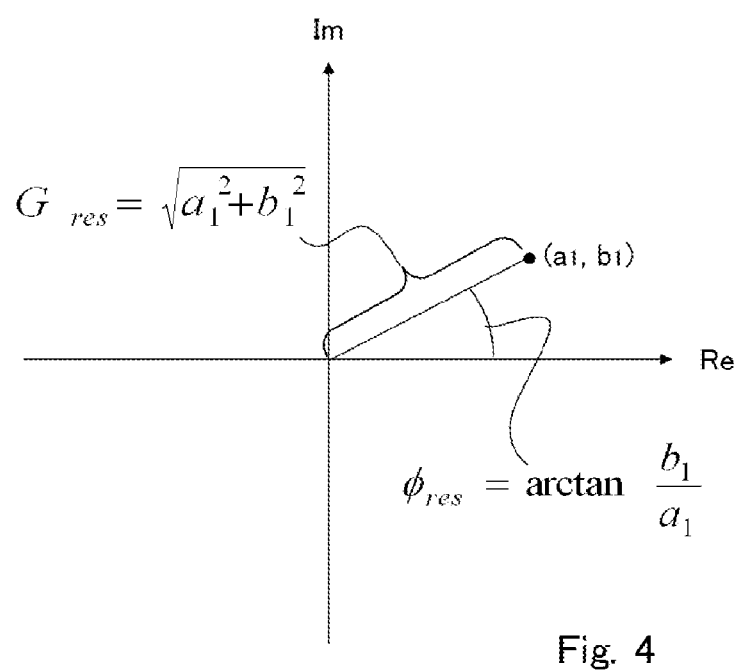
FIG. 4 is a complex plane graph representing the relationship among the gain and the phase when in a respiratory induction apparatus according to Embodiment 1 of the present invention, a respiratory signal is evaluated by utilizing an evaluation function.
Figure 5:
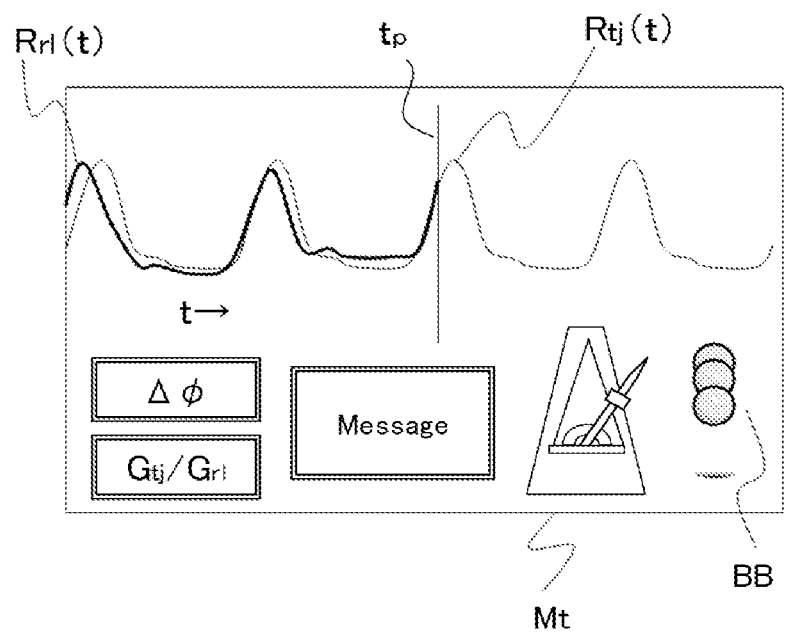
FIG. 5 is a chart representing an example of display screen displayed when respiration is induced in the respiratory information instruction apparatus of a respiratory induction apparatus according to Embodiment 1 of the present invention.
Figure 6:
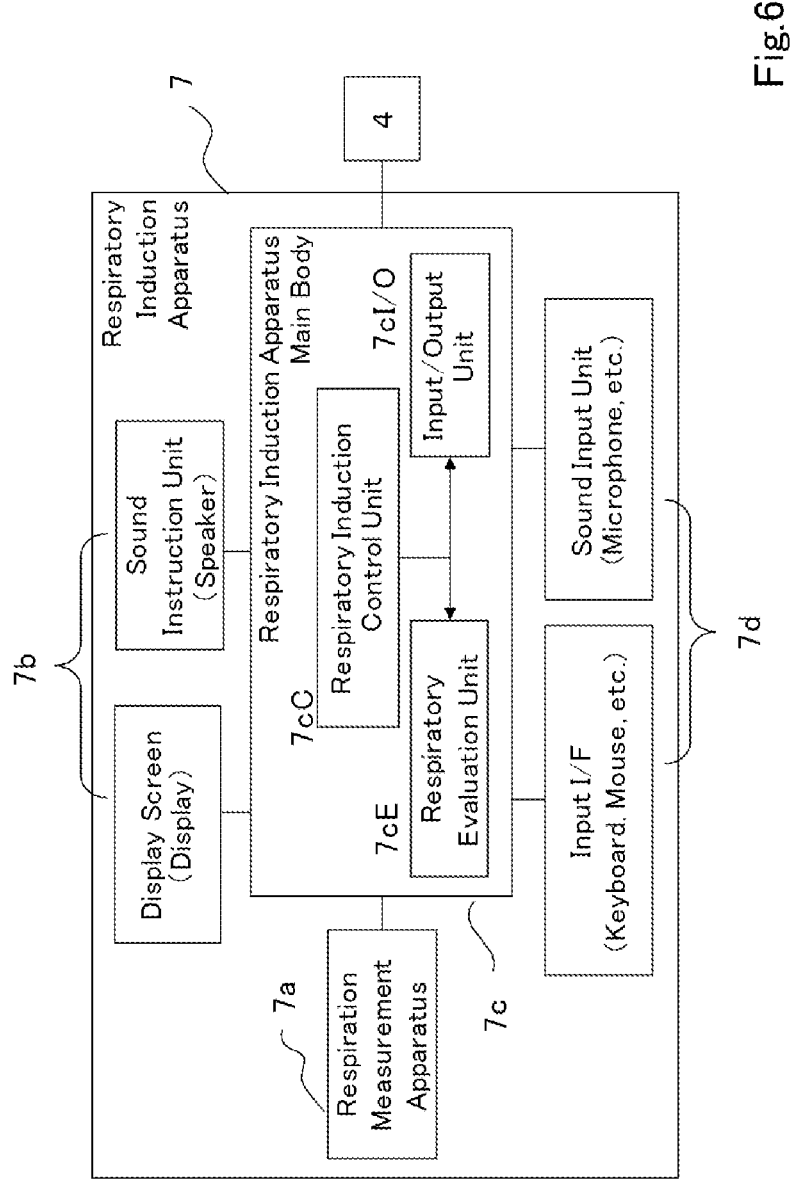
FIG. 6 is a block diagram for explaining the configuration of a respiratory induction apparatus according to Embodiment 1 of the present invention.
Figure 7:
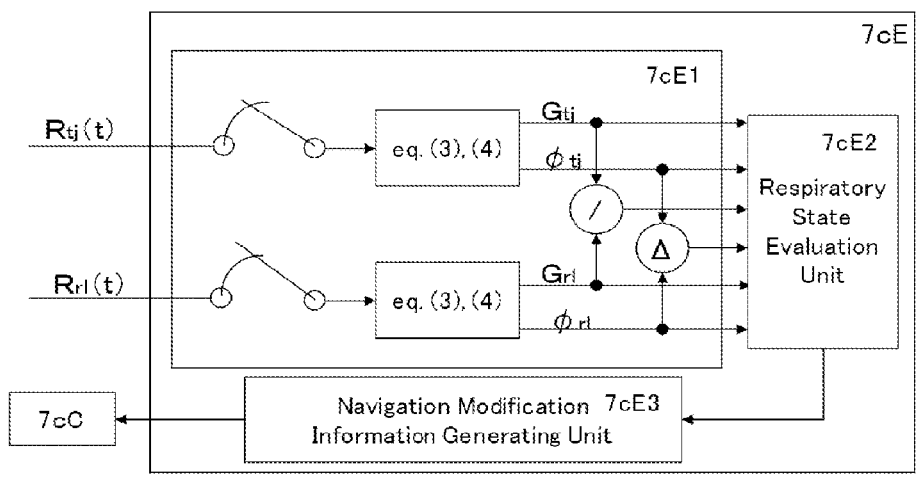
FIG. 7 is a block diagram for explaining the configuration of a respiration evaluation unit of a respiratory induction apparatus according to Embodiment 1 of the present invention.
Figure 8:
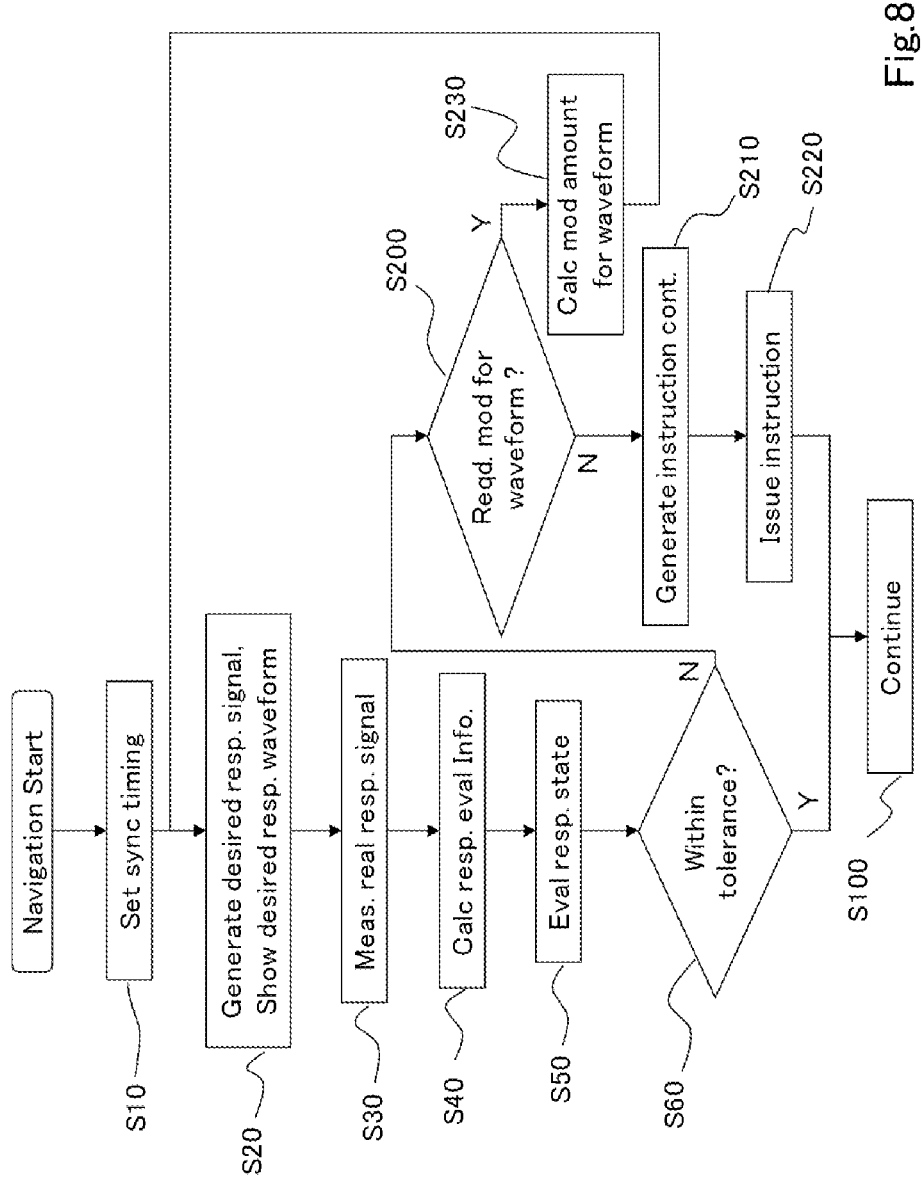
FIG. 8 is a flowchart for explaining the operation of a respiratory induction apparatus according to Embodiment 1 of the present invention and the operation of a respiratory induction program according to Embodiment 2.

The configuration of a respiratory induction apparatus (respiratory navigation apparatus) according to Embodiment 1 of the present invention and the configuration of a particle beam therapy system provided with the respiratory induction apparatus will be explained below. FIGS. 1 through 7 are to explain the configurations of a respiratory induction apparatus and a particle beam therapy system according to Embodiment 1 of the present invention; FIG. 1 is a diagram illustrating the whole configuration of a particle beam therapy system; FIG. 2 is a functional block diagram for explaining the configuration related to control of a particle beam therapy system; FIG. 3 is a waveform chart representing the relationship among a (desired) respiratory signal, an evaluation function, and a respiration gate signal; FIG. 4 is a complex plane graph representing the relationship among the gain and the phase when a respiratory signal is evaluated by utilizing an evaluation function; FIG. 5 is a chart representing an example of display screen displayed when respiration is induced in the respiratory information instruction apparatus included in a respiratory induction apparatus. FIG. 6 is a block diagram for explaining the configuration of a respiratory induction apparatus; FIG. 7 is a block diagram for explaining the configuration of the respiration evaluation unit of a respiratory induction apparatus; FIG. 8 is a flowchart for explaining the operation of a respiratory induction apparatus.

At first, the configuration of a particle beam therapy system will be schematically explained with reference to FIG. 1. In FIG. 1, a particle beam therapy system is provided with a circular accelerator (just referred to as an accelerator, hereinafter) 1, which is a synchrotron as a supply source of a charged particle beam; an irradiation system 2 equipped with irradiation apparatuses provided in respective treatment rooms; a transport system 3 that connects the accelerator 1 with each treatment room and transports a charged particle beam from the accelerator to the irradiation apparatus in each treatment room; and a control system 4 that cooperatively controls these systems (subsystems, described later). The particle beam therapy system according to the present invention is characterized in that in a respiratory induction apparatus provided in each of the treatment room, data on a real respiratory signal is acquired in synchronization with the period of a desired respiratory signal whose period is specified; from the coefficients of a pair of trigonometric functions corresponding to the first term by means of Fourier series expansion of the data, a phase, which is a temporal position of the real respiratory signal and a gain, which is a depth thereof are derived; as a result, it is made possible to quantitatively compare the real respiratory signal with the desired respiratory signal for the purpose of performing respiratory induction. Explaining in detail later about the quantitative comparison and control based on the result of the comparison, the configurations will be explained now.

<Accelerator>

The accelerator 1 is provided with a vacuum duct 11 that serves as an orbit path through which a charged particle beam circulates; an injector 12 for injecting a charged particle beam, supplied from a prestage accelerator 5, into the vacuum duct 11; deflection electromagnets 13a, 13b, 13c, and 13d (collectively referred to as 13) for deflecting the orbits of charged particles so that the charged particles form a charged particle beam that circulates along a circulation orbit in the vacuum duct 11; convergence electromagnets 14a, 14b, 14c, and 14d (collectively referred to as 14) for converging a charged particle beam formed on the circulation orbit not to diverge; a high-frequency wave acceleration cavity 15 that applies a high-frequency voltage, synchronized with circulating charged particles, to the circulating charged particles so as to accelerate the charged particles; an emission apparatus 16 for extracting from the accelerator 1 a charged particle beam accelerated in the accelerator 1 and emitting the extracted charged particle beam into the transport system 3; and a six-pole electromagnet 17 that excites resonance in the circulation orbit of a charged particle beam in order to make the emission apparatus 16 emit the charged particle beam.

There are provided unillustrated apparatuses for controlling the respective units; for example, in the deflection electromagnet 13, there is provided a deflection electromagnet control apparatus that controls the excitation current for the deflection electromagnet 13, and in the high-frequency wave acceleration cavity 15, there are provided a high-frequency wave source for supplying a high-frequency voltage to the high-frequency wave acceleration cavity 15 and a high-frequency wave control apparatus for controlling the high-frequency wave source; in the control unit 4, there is provided an accelerator control apparatus 41 that controls the whole accelerator 1 by controlling other components such as the deflection electromagnet control apparatus, the high-frequency wave control apparatus, and convergence electromagnet 14. However, in the technical idea of the present invention, the control of the accelerator 1 itself is not limited; therefore, the accelerator is not limited to the one having the foregoing configuration, and it goes without saying that various modifications are allowed, as long as the variants can stably emit a charged particle beam into the transport system 3.

In FIG. 5, for the sake of simplicity, the prestage accelerator 5 is illustrated as if it is a single apparatus; however, in practice, the prestage accelerator includes an ion source (ion beam generator) that generates a charged particle (ion) such as a proton or a carbon ion particle (heavy ion particle) and a linear accelerator system that performs initial acceleration of a generated charged particle. A charged particle injected from the prestage accelerator 5 to the accelerator 1 is accelerated in a high-frequency electric field up to 70% to 80% of the light velocity, as it is being bent by means of the magnets.

<Transport System>

The charged particle beam accelerated by the accelerator 1 is emitted to the transport system 3, which is referred to as an HEBT (High Energy Beam Transport) system. The transport system 3 is provided with a vacuum duct (a main duct 31m, a treatment-room-A duct 31A, and a treatment-room-B duct 31B: collectively referred to as a vacuum duct) 31; a switching electromagnet 32, which is a switching device for switching the orbits of a charged particle beam; and a deflection electromagnet 33 that deflects a beam at a predetermined angle. The charged particle beam that has been sufficiently energized by the accelerator 1 and travels through the transport path formed of the vacuum duct 31 is led to the irradiation apparatus provided in a designated treatment room; the orbit of the charged particle beam is changed (to the 31A direction or to the 31B direction) by the switching electromagnet 32, as may be necessary.

<Irradiation System>

The irradiation system 2 includes an irradiation apparatus 21 that forms a charged particle beam supplied from the transport system 3 into an irradiation field conforming to the size or the depth of a diseased site of a patient as an irradiation subject and a respiratory induction apparatus 7 having a respiratory navigation function of inducing respiration at a time when irradiation is performed. In conjunction with respiratory induction and real respiration, the on/off of irradiation onto a diseased site as an irradiation subject is controlled (in accordance with the phases of a desired respiratory signal and a real respiratory signal). As described "the irradiation apparatus provided in a designated treatment room" in the explanation for the transport system, a particle beam therapy system, in general, is provided with a plurality of treatment rooms (in FIG. 1, treatment rooms 6A and 6B are collectively referred to as a treatment room 6) in view of the therapy efficiency. In other words, in the irradiation system 2, the irradiation apparatus 21 and the respiratory induction apparatus 7 are provided in each treatment room 6; for example, an irradiation system 2A for the treatment room 6A includes an irradiation apparatus 21A and a respiratory induction apparatus 7A.

In order to realize a respiratory navigation (hereinafter, although referred to as "respiratory induction", as far as the configuration of an apparatus is concerned, it is also referred to as "respiratory navigation", which is a generally used term, in the case where it is utilized alone) function, the respiratory induction function 7 is provided with a respiration measurement apparatus 7a for measuring the respiratory state of a patient; a respiratory induction apparatus main body 7c for determining whether or not particle-beam irradiation onto a patient should be implemented, based on a real respiratory waveform measured by the respiration measurement apparatus 7a and a desired respiratory waveform for inducing respiration, and for managing the whole respiratory induction apparatus 7; and a respiratory information instruction apparatus 7b for giving instructions to a patient about information on respiration synchronization. In particular, with regard to evaluation of the respiratory state, the respiratory induction apparatus 7c, as described later, is provided with a respiration evaluation unit 7cE that quantitatively evaluates the respiratory state, based on the phase and the amplitude (gain) mathematically calculated from a real respiratory waveform and the desired respiratory waveform for performing respiratory induction and that determines whether or not the respiratory induction should be modified, based on the result of the evaluation.

<Treatment Room>

In FIG. 1, in the treatment room A (6A), the whole irradiation including the deflection electromagnet 33G through the irradiation apparatus 21A is a rotating irradiation room that revolves around a patient (treatment table) so that the angle of particle beam irradiation onto the patient can freely be rotated; the rotating irradiation room is referred to also as a rotating gantry. The treatment room B (6B) is a horizontal irradiation room in which a particle beam is horizontally irradiated from the irradiation apparatus 21B onto a patient who is seated on a chair whose angle and position can freely be set. As an example, there have been described two treatment rooms whose types are different from each other; however, one and the same respiratory navigation function can be applied to the treatment rooms, regardless of the types of the treatment rooms. Accordingly, even though the type of a treatment room is different from that of the treatment type described above, or even though the number of treatment rooms is different from that of the treatment rooms described above, one and the same respiratory navigation function can be applied to those treatment rooms <Control System>

In many cases, a control system for such a large-size complex system configured with a plurality of subsystems, in general, includes a sub-controller that is dedicated to control of each subsystem and a main controller that conducts and controls the whole system. This configuration with a main controller and a sub-controller is adopted also in the control system 4 for a particle beam therapy system according to Embodiment 1 of the present invention. For the sake of simplicity, there will be explained a control system, among control systems for a particle beam therapy system, which relates to the control of three subsystems, i.e., the accelerator 1, the transport system 3, and the irradiation system 2; in other words, there will be explained the control system 4 provided with the accelerator control unit 41, a transport system control unit 43, an irradiation system control unit 42, and a whole system control unit 40, as illustrated in FIG. 1.

The control system 4 will be explained with reference to FIG. 2, which schematically illustrates the configuration of the control system. Meanwhile, in general, as the controller of a particle beam therapy system, a workstation or a computer is utilized. Accordingly, in many cases, the controller is referred to as a "computer". For example, the main controller 40 in FIG. 2 is, in fact, a function of a computer, which is, in many cases, referred to as an irradiation system common computer; however, the main controller 40 is dealt with as a controller having a specific function. The apparatus control computer corresponds to a sub-controller 42 that controls the irradiation system 2, which is a subsystem; the portions thereof corresponding to the respective controllers for the irradiation systems 2A and 2B that are separately arranged in the treatment rooms 6A and 6B are designated as 42A and 42B, respectively. As described above, the particle beam therapy system 4 is provided with the main controller 40 and the sub-controllers 41, 42, and 43, which are controllers for the accelerator 1, the irradiation system 2, and the transport system 3, respectively.

The sub-controllers 41, 42, and 43 perform control operations in a collaborative manner, based on a timing instruction function provided in the main controller 40. The timing instruction function itself may be the one that outputs a timing signal for synchronization. The respective positions and the like of the sub-controllers in FIGS. 1 and 2 differ from each other; this is because in FIG. 1, the controller 4 is illustrated as a whole, which has a control function, and in FIG. 2, the sub-controllers are illustrated with respect to the control subjects; thus, that does not represent the matter as to whether or not the physical positions are different from each other. In other words, it is not substantial matter how physically arranged the sub-controllers are. Additionally, there will be explained later a program to be installed in the computer in order to configure these sub-controllers and the configuration of modules and the like in the program.

The respective "consoles" connected with the apparatus control computers (the sub-controllers 42A and 42B) are each a keyboard, a display, or the like or a terminal such as a controller box; in other words, it is a man-machine interface. Consoles are provided in the treatment room 6 and an irradiation operation room that is provided separately from the treatment room, in many cases. A control board is connected at a lower hierarchical level than the apparatus control computer is connected. Specifically, as described in parentheses, the control boards is the driver, the amplifier, the PLC (Programmable Logic Controller), or the like for each of the apparatuses. Apparatuses are connected at a further lower hierarchical level than the control board is connected. The apparatuses include a motor for moving the respective axes of a treatment table, a motor for driving the X-ray image-capturing device in the irradiation apparatus, and the like; in general, the irradiation apparatus 21 and the respiratory induction apparatus 7, described above, are also included. Additionally, in the rotating-gantry treatment room 6A, the apparatuses also include a motor related to the control of the rotation position and the like of the whole irradiation system.

In the case of the particle beam therapy system according to Embodiment 1, the navigation function unit 7 is directly controlled by the main controller 40, without involving the control board provided in the treatment room 6. This is because, as described later, the respiratory state in the particle beam therapy system according to Embodiment 1 can be quantitatively evaluated, and hence, because in particular, the respiratory phase can accurately be grasped, the real advantage can further be demonstrated not only in the case where respiratory navigation is optimized in a single treatment room, but also in the case where cooperative control is performed such as performing respiratory induction in synchronization with the operation cycle of the accelerator or synchronizing the respiratory induction in one treatment room with the respiratory induction in the other treatment room. This is because by further reducing the number of apparatuses involved, the timing difference caused by the occurrence of wasteful time (delay) can be prevented and hence the cooperative control can smoothly be performed. In this regard, however, the direct connection is not the indispensable condition; it goes without saying that in the case of the cooperative control, the way of connection may appropriately be changed as long as the timing can be ensured.

The other role of the irradiation system common computer (main controller 40) is to conduct the whole particle beam therapy system, as described above; in some cases, as the controller for an apparatus that requires control synchronizes with the accelerator 1 and the transport system 3, the irradiation system common computer undertakes some of the functions of the sub-controller 42. That is why in FIG. 1, reference numeral 42 is in parentheses.

As described above, the control function, related to the respiratory induction apparatus 7, out of the control functions of the sub-controller 42 is undertaken by the main controller 40. The apparatuses such as a motor for moving the respective axes of a rotating gantry and a treatment table and a motor for driving the X-ray image-capturing device in the irradiation apparatus are controlled by the intermediary of the sub-controller 42, as usual. The motor for the gantry and the treatment table and the motor for the X-ray image-capturing device are not moved when a beam is being irradiated. That is to say, this is because it is not required to implement control in synchronization with the accelerator system 1 and the transport system 3. In order to exchange information about their conditions, the irradiation system common computer (main controller 40) and the irradiation system apparatus control computer (sub-controller 42) communicate with each other, for example, by use of a Ready signal that indicates in which treatment room 6 the irradiation system 2 has completed its positioning and is ready to irradiate a beam, a signal that indicates in which treatment room 6 the irradiation system 2 has irradiated a beam and completed its irradiation. Briefly speaking, it is regarded as carrying out events sequentially. In other words, in terms of relationship with the sub-controller 42, the role of the irradiation system common computer (main controller 40) is to perform irradiation management with regard to, for example, "which irradiation systems 2 in the respective treatment rooms 6 contend with one another for a beam from the accelerator"; once it is determined which irradiation systems 2 in the respective treatment rooms 6 contend with one another for a beam from the accelerator, the sub-controller 42 in each treatment room 6 can determine the sequence.

However, as described later, in some cases, respiratory induction is controlled in such a way as to be synchronized with the respiratory induction in another treatment room or the operation cycle of the accelerator, in order to make good use of the characteristics of the particle beam therapy system, according to Embodiment 1 of the present invention, that can appropriately navigate the respiration. In other words, in the case where the sequence cannot be determined by the sub-controller of each treatment room alone, it is desirable that the command value to the respiratory induction apparatus 7 is transmitted not from the apparatus control computer (sub-controller 42) but from the irradiation system common computer (main controller 40) directly.

Meanwhile, among the functions of the irradiation system 2, the function of forming an irradiation field is not the essential part of the present invention. Accordingly, the description about the configuration of the irradiation apparatus 21 will be omitted. In contrast, the beam gate, which on/off-controls the irradiation onto an irradiation subject in conjunction with the respiratory navigation, requires synchronization with the transport system 3; therefore, although not illustrated in FIG. 2, the beam gate is directly controlled by the main controller 40. Furthermore, the wobbler electromagnet or the scanning electromagnet, which requires the control synchronized with the accelerator system 1, is also an apparatus included in the irradiation apparatus 21; thus, for the same reason, the wobbler electromagnet or the scanning electromagnet is directly controlled by the irradiation system common computer 40.

<Quantitative Evaluation of Respiration>

By providing the foregoing configuration, it is made possible to form a so-called pencil-like particle beam supplied from the accelerator into an irradiation field corresponding to the position and the shape of an irradiation subject and then to irradiate it. In contrast, in the case where the irradiation subject is shifted through respiration, it is required to measure the respiratory state through the respiratory navigation function and then to perform control in such a way that a particle beam is irradiated at a respiratory phase where the position and the shape stabilize. Here, the problem is how the respiratory state, which is the reference of control, is quantitatively evaluated. Because the objective of the respiration evaluation is to evaluate the displacement of an irradiation subject, the evaluation items are the delay or advance (timing difference) with respect to an induced rhythm (desired respiratory waveform) and the difference in the size (depth).

It is conceivable that respiration is basically a periodic movement; thus, based on a respiratory waveform, which is the temporal change of a respiratory signal measured by a respiration sensor or the like, the period, phase, and amplitude thereof are evaluated so that the respiration can quantitatively be evaluated. However, as described in "Background Art", in conventional respiratory navigation, the phase and the gain of the respiratory waveform are evaluated only at the position, in a respiratory waveform, at which the respiratory waveform becomes maximum or minimum, or becomes above a threshold value or below the threshold value. In other words, only a specific position of the respiratory waveform, such as "peak to peak", is an evaluation subject; therefore, even when a patient is choked in process of the evaluation, such a state cannot be evaluated. Furthermore, for example, in the case where due to intrusion of noise, multiple peaks are appeared in a respiratory waveform, in the case where due to displacement of the posture of a body, an offset changes, or in the case where the sensor is saturated and hence there is caused a portion that indicates a constant value, the evaluation itself may become impossible.

On the other hand, in general, the period of human respiration is not constant, and the length of the respiration depends on individuals. Furthermore, because a respiratory waveform is not a complete sine wave, it is difficult to obtain a desired phase or gain, even though mathematical processing is applied to the whole respiratory waveform. However, by applying appropriate processing to the respiratory waveform in accordance with the characteristics of respiration, it is made possible to mathematically evaluate unstable respiration. Accordingly, in the present invention, attention has been focused on the characteristic that although controlled by the autonomic nerves, respiration, exceptionally, can consciously be performed, and hence respiration, which is usually irregular, can at least be induced to a constant period, by, as in a respiratory navigation apparatus, indicating a predetermined rhythm (desired respiratory waveform) so as to perform respiratory induction. In other words, it was found that in the case where respiratory induction is performed, by assuming a real respiratory waveform as a waveform having the same period as that of the desired respiratory waveform utilized for the respiratory induction, mathematical evaluation, described later, can be performed; then, it has been made possible to quantitatively evaluate the phase and the amplitude of the real respiratory waveform.

Here, in order to make the explanation for the present invention clear and for the purpose of mathematically processing a respiratory waveform (respiratory signal forming the respiratory waveform), some terms and important notions will be precisely defined.

<Respiratory Signal, Desired Respiratory Signal, and Real Respiratory Signal>

Respiratory Signal R(t):

A signal that indicates the state of respiration; by measuring, through a sensor, the expiration movement, temperature change due to expiration, movement of, for example, an abdomen due to respiration, and the like, the respiratory state can be obtained as a signal. Specifically, there are conceivable a method of detecting the flow of expired air by means of a flow sensor, a method of measuring the temperature change, due to inspiration, in the vicinity of nasal cavities through image processing by a thermistor or an infra-red camera, a method of detecting the abdominal movement of a patient by means of a position sensitive detector (position sensor) that senses a laser-beam source mounted on the abdomen, and a method of converting the abdominal movement of a patient into a signal by means of a laser displacement gauge. A respiratory waveform represents the temporal change of this respiratory signal. In performing respiratory induction, a signal that serves as a desired signal will be referred to as a desired respiratory signal, and a waveform that represents the temporal change of the desired respiratory signal will be referred to as a desired respiratory waveform. In order to make the explanation clear, the desired respiratory signal will be expressed by $R_{tj}(t)$ with a subscript "tj" (abbreviation of trajectory), and the real respiratory signal will be expressed by $R_{rl}(t)$ with a subscript "rl" (abbreviation of real).

<Obtaining of Desired Respiratory Signal>

In particle beam therapy in which a respiratory navigation apparatus is utilized, roughly two stages are required. One stage is to obtain a desired respiratory signal, and the other stage is to perform treatment by utilizing the desired respiratory signal. The real respiratory signal at the stage of treatment, i.e., the evaluation subject at a time when respiratory induction is performed is a real respiratory signal $R_{rl}(t)$ obtained by measuring the respiratory state of a patient at a time when respiratory induction is performed based on the desired respiratory signal $R_{tj}(t)$. However, the desired respiratory signal $R_{tj}(t)$ itself is obtained based on a so-called real respiratory signal (referred to as a preliminary real respiratory signal, hereinafter) obtained by measuring the respiration of a patient prior to the treatment.

The stage at which a desired respiratory signal is obtained will be explained. A desired respiratory signal may be obtained through a method similar to any method that is commonly implemented; for example, it can be obtained through the method disclosed in Paragraphs 0031 through 0037 of Patent Document 6. In this regard, however, in the case of respiratory induction in a particle beam therapy system according to Embodiment 1 of the present invention, a desired respiratory signal is not only utilized for setting the timing of respiratory induction but also, as described later, utilized as a comparison subject when the phase and the amplitude of a real respiratory signal is quantitatively evaluated in a mathematical manner; therefore, the following points should strictly be observed.

<Points to be Strictly Observed when Desired Respiratory Signal is Obtained>

1. A preliminary real respiratory signal is obtained by utilizing the same sensor and through the same method as when a real respiratory signal at a time when treatment is measured.

2. Expansion/contraction processing and truncation processing are implemented in order to perform necessary averaging processing and to adjust the period.

3. In principle, a desired respiratory signal is generated from the preliminary real respiratory signal of a patient himself to be treated.

Exceptionally, a desired respiratory signal may be generated based on the respiratory signal of another person, or generated artificially. In this case, however, it is required to utilize a respiratory signal whose respiratory behavior can be regarded as being the same as that of a patient to be treated; in the case where there is produced a predetermined difference in the gain or the phase, described later, it is required that the value is held as a correction value so that in the evaluation of the respiratory state, the "predetermined difference" can be taken into consideration. In Embodiment 1, the respiratory navigation apparatus shows the desired respiratory signal $R_{tj}(t)$ generated (obtained) in this manner, at a timing synchronized with the accelerator.

Next, there will be defined parameters for evaluating the respiratory signals defined, as described above, with regard to respiration and respiratory induction.

<Frequency and Period of Respiration>

Period of Respiration $T_{res}$:

A broad-sense respiratory period denotes the time in which one period of "inspiration to expiration" is performed. As the desired respiratory signal $R_{tj}(t)$ for respiratory navigation in the respiratory induction apparatus according to Embodiment 1 of the present invention, there is utilized a signal that has a predetermined period and can be represented by a periodic function ($f(t)=f(t+T)$). Accordingly, a narrow-sense respiratory period denotes the period T of this periodic signal. That is to say, the narrow-sense respiratory period denotes the time corresponding to one period of the periodic desired respiratory signal $R_{tj}(t)$. As the unit, [sec], which is a typical unit for time, is utilized.

Frequency of Respiration $F_{res}$:

This is the reciprocal ($F_{res}=1/T_{res}$) of the period $T_{res}$ of respiration. The unit thereof is [1/sec]. The frequency obtained by multiplying the frequency of respiration by $2\pi$ ($\omega_{res}=2\pi F_{res}$) is referred to as the angular frequency of respiration.

<Gain and Phase of Respiration, Describing Function>

Gain of Respiration $G_{res}$:

The gain of the respiratory signal R(t) is simply referred to as a "gain of respiration". The gain referred to here should strictly be defined. Provided the respiratory signal R(t) is given by a trigonometric function, the gain thereof is so-called an amplitude.

$$G_{res}=A, \text{ if } R(t)=A\cos(\omega_{res}t+\phi_{res})$$

Phase of Respiration $\phi_{res}$:

The phase of the respiratory signal is simply referred to as a "phase of respiration". Mathematically, the phase of respiration denotes phase advance with respect to $\cos(\omega_{res}t)$ in the above equation; as the unit, [radian] or [angle (°)], which is a unit for angle, is utilized. In addition, the situation contrary to "phase advance" is expressed as "phase delay".

However, as described above, no respiratory signal R(t) is complete trigonometric function. In this regard, however, because at least the desired respiratory signal $R_{tj}(t)$ is a signal of a constant period, there will be considered a method in which the desired respiratory signal $R_{tj}(t)$ is transformed into a trigonometric function that is closest to the desired respiratory signal $R_{tj}(t)$, and then the gain and phase thereof are calculated. Thus, assume that the desired respiratory signal $R_{tj}(t)$ is represented in the Fourier series expansion form, as expressed in the equation (1); a pair of coefficients $a_1$ and $b_1$, of the trigonometric function, which correspond to the 1st-order term among the 0th-order term through nth-order term of the equation (1), are calculated as expressed in the equation (2); then, the calculated coefficients $a_1$ and $b_1$ are specified as the describing functions that indicate the state of the respiratory signal. In other words, there are calculated the coefficients $a_1$ and $b_1$ of the cosine function and the sine function that configure the fundamental waveform component that is obtained by removing the constant term and the high-frequency components from the desired respiratory waveform. FIG. 3 represents a describing function formed of $a_1$ and $b_1$ obtained from the desired respiratory signal $R_{tj}(t)$ and the equation (2).

$$R(t) = \frac{a_0}{2} + \sum_{n=1}^{\infty}(a_n\cos(n\omega_{res}t) + b_n\sin(n\omega_{res}t)) \quad (1)$$

$$\left.\begin{array}{l}a_1 = \dfrac{1}{\pi}\displaystyle\int_0^{2\pi} R(t)\cos(\omega_{res})d\omega_{res}t \\ b_1 = \dfrac{1}{\pi}\displaystyle\int_0^{2\pi} R(t)\sin(\omega_{res}t)d\omega_{res}t\end{array}\right\} \quad (2)$$

As represented in the equations (3) and (4), the gain $G_{res}$ and the phase $\phi_{res}$ can be obtained respectively from $a_1$ and $b_1$ that form the describing function extracted as described above. FIG. 4 represents the relationship on a complex plane between the gain $G_{res}$ and the phase $\phi_{res}$, of the desired respiratory signal $R_{tj}(t)$, that are obtained from the coefficients $a_1$ and $b_1$.

$$G_{res} = \sqrt{a_1^2 + b_1^2} \quad (3)$$

$$\phi_{res} = \arctan\frac{b_1}{a_1} \quad (4)$$

<Integration Range and Calculation Frequency>

The reason why as described above, it is made possible to calculate the gain $G_{res}$ and the phase $\phi_{res}$ by mathematically extracting the describing function from the desired respiratory signal $R_{tj}(t)$ is that the desired respiratory signal $R_{tj}(t)$ is a periodic function having a constant angular frequency $\omega_{res}$. According to the equation (2), the integration range $\omega_{res}$ necessary for the calculation of the gain and phase is from 0 to $2\pi$. That is to say, t is from 0 to $2\pi/\omega_{res}$ ($=T_{res}$); thus, the respiration period $T_{res}$ is the integration range necessary for the calculation, i.e., the calculation unit.

In contrast, the real respiratory signal $R_{rl}(t)$ is irregular signal, as described above. However, when respiratory induction is performed based on the desired respiratory signal $R_{tj}(t)$, the real respiratory signal $R_{rl}(t)$ also becomes a periodic function having the same period as that of the desired respiratory signal $R_{tj}(t)$. By utilizing the respiratory characteristics thereof, as is the case with the desired respiratory signal $R_{tj}(t)$, also with regard to the real respiratory signal $R_{rl}(t)$, there can be calculated a describing function including the pair of coefficients $a_1$ and $b_1$, of the trigonometric functions, that correspond to the 1st-order terms by means of Fourier series expansion, as represented in the equation (2), of the real respiratory signal $R_{rl}(t)$.

It is assumed that in respiratory navigation, the desired respiratory signal $R_{tj}(t)$ is shown at a timing synchronized with that of the accelerator so that, for example, a particle beam is efficiently utilized. In this case, it is required not only to grasp the real respiration but also to synchronize the respiration of a patient with a predetermined timing. Accordingly, the desired respiratory signal $R_{tj}(t)$ outputted from the apparatus and the real respiratory signal $R_{rl}(t)$ obtained by measuring the real respiratory state of a patient are displayed in such a way that as represented in FIG. 5, the respective past portions and future portions thereof are distinguished from each other at the present time point $t_p$ on the common temporal axis. When respiratory navigation is performed in such a manner as described above, the real respiratory signal $R_{rl}(t)$, which is usually irregular, can be regarded as a function of the same respiration period $T_{res}$ as that of the desired respiratory signal $R_{tj}(t)$, as represented in FIG. 5. Thus, the respective gains $G_{tj}$ and $G_{rl}$ and the respective phases $\phi_{tj}$ and $\phi_{rl}$ can also be calculated based on the common temporal axis "t". In other words, each of the foregoing equations is utilized, by setting, as the integration range (calculation window), one period $T_{res}$, on the common temporal axis which is the basis of the timing synchronized with that of the accelerator.

In this situation, there are conceivable roughly two frequencies at which the respective gains $G_{tj}$ and $G_{rl}$ and the respective phases $\phi_{tj}$ and $\phi_{rl}$ of the desired respiratory signal $R_{tj}(t)$ and the real respiratory signal $R_{rl}(t)$ are calculated. In the first case, they are calculated every respiration period $T_{res}$ on the common temporal axis, and the calculation window in this case begins at a given phase in the period; for example, when the start of the period (phase "0") is set as the starting point, the calculation window is always the period from 0 to $2\pi$. In the second case, they are calculated every sampling period; in this case, the calculation window is from (sampling time point$-2\pi$) to (sampling time point).

In the first case, the calculation window appears every respiration period and always begins at the phase "0". In the second case, the window whose length is the respiration period $T_{res}$ is slid in such a way as to always ends at the present time point. The required phase is a relative value to the desired respiratory signal; because in each of the foregoing equations, the starting point of the calculation window may be set anywhere, calculation can be performed in either case. In contrast, in the case where as in a conventional case, the phase is obtained from the singular point in the period, the starting point of the evaluation needs to be set with respect to the singular point; therefore, the evaluation can only be performed every respiration period.

Additionally, in the explanation for the second case, it has been described that "the calculation is performed every sampling period". "Sampling" denotes discrete-time extraction of a signal from a signal that changes in a continuous-time manner. The equation (2) represents a continuous-time equation; however, in practice, calculation is implemented in a discrete-time manner. That is because in general, a computer that performs this kind of calculation can deal with a signal only in a discrete-time manner.

Next, the specific method for the respiratory navigation utilizing the respiratory signals, the definitions thereof and the evaluation methods therefor are determined in such a manner as described above, will be explained with reference to FIG. 5, which has been utilized in the foregoing explanation, and the functional block diagram for evaluating the respiratory signal.

The desired respiratory signal is designed in such a way as to have a desired period $T_{res}$, based finally on the specification of the accelerator and the like. Then, the gain $G_{tj}$ and the phase $\phi_{tj}$ of the set desired respiratory signal $R_{tj}(t)$ are obtained by use of the equations (3) and (4). As a result, the size and the timing of the set desired respiratory signal $R_{tj}(t)$ itself can be quantified; for example, in a respiration evaluation unit 7c2, described later, the quantified desired respiratory signal $R_{tj}(t)$ can be a reference (comparison subject) for quantitatively evaluating a real respiratory signal.

<Specific Method for Respiratory Navigation>

When it appeals to the sense of hearing as well as to the sense of eyesight, the effect thereof can further be demonstrated. Specifically, instruction is given by the sound "expire" or "inspire". More effect is demonstrated when as illustrated in FIG. 5, the sound of a metronome is added to the foregoing sound instruction. The desired respiratory signal $R_{tj}(t)$ utilized in the particle beam therapy system according to Embodiment 1 is designed with a planned desired period $T_{res}$; then, the gain $G_{tj}$ and the phase $\phi_{tj}$ of the desired respiratory signal $R_{tj}(t)$ are obtained by use of the equations (3) and (4). Based on the respiration period $T_{res}$ and the phase (information) calculated from one-period signal, the metronome sound can be added. The metronome sound is made, for example, by dividing the respiration period $T_{res}$, which is regarded as one bar, into eighth notes; in other words, the sound is made every time when the phase of the desired respiratory signal $R_{tj}(t)$ advances by 45°. It is desirable that the respiratory induction apparatus displays a bouncing ball BB in conjunction with the metronome sound. A bouncing ball is an animation in which a ball moves in conjunction with a metronome. The animation means is not limited to a bouncing ball; any means can be utilized, as long as the metronome Mt can be visualized.

In that case, at the stage of real treatment, as represented in FIG. 5, the waveforms of the desired respiratory signal $R_{tj}(t)$ and the real respiratory signal $R_{rl}(t)$ of a patient are displayed with a common temporal axis so that the past and the future are distinguished from each other and are shown to the patient. This method is disclosed, for example, in the paragraphs 0038 through 0045 of Patent Document 6; with this method, the patient can readily be aware of the difference between the desired respiratory signal and his own respiratory state and hence he can easily synchronize his own respiratory state with the desired respiratory signal. However, because among patients, there are many elderly people, it is not necessarily easy to recognize the difference and modify the respiratory state; therefore, there has been a problem that there is required a direct instruction for the modification. Accordingly, furthermore, in the respiratory induction apparatus and the particle beam therapy system according to Embodiment 1 of the present invention, the gain and the phase of the respiratory signal are quantitatively calculated and based on the calculated gain and phase, the modification instruction is issued.

FIG. 6 is a diagram for explaining the configuration of the respiratory induction apparatus provided in each of the treatment rooms in the particle beam therapy system according to Embodiment 1. In FIG. 6, the respiratory induction apparatus 7 is provided with a respiratory induction apparatus main body 7c; a respiration measurement apparatus 7a, which is referred to also as a respiration synchronization sensor for measuring the respiratory (signal) of a patient; a respiratory information instruction apparatus 7b having a display, which is a display screen for showing a patient the foregoing information on the respiration synchronization, and a speaker, which is a sound-or-the-like instruction unit for performing transmission through the sense of hearing; and an interface 7d having a keyboard and a mouse, which are input I/Fs for an operator of the respiratory navigation apparatus to perform setting, related to respiratory induction, such as selecting a layout on the display screen and to perform communication with the apparatus, and a microphone or the like, which is a sound-or-the-like input unit for supplementarily inputting the foregoing sound-or-the-like instruction to the apparatus.

The respiratory induction apparatus main body 7c is provided with an input/output unit 7cI/O that inputs an information signal from and outputs an information signal to the particle beam therapy system; for example, in the case where respiratory induction (respiratory navigation) is started based on input information from the interface 7d, desired respiratory signal data for at least one period is obtained, as a desired respiratory waveform necessary for the respiratory induction, from a data base of the treatment planning apparatus in the particle beam therapy system. After that, the desired respiratory signal $R_{tj}(t)$ is generated in such a way that the obtained desired respiratory waveform is synchronized with the accelerator in the particle beam therapy system and is displayed by the respiratory information instruction apparatus 7b; concurrently, the respiration measurement apparatus 7a measures the real respiratory state of a patient, and the measured real respiratory signal $R_{rl}(t)$ is obtained.

As illustrated in FIG. 7, a respiration evaluation unit 7cE provided in the respiratory induction apparatus main body 7c is provided with a respiration evaluation information calculation unit 7cE1 that, by use of the equations (3) and (4), calculates the respective gains $G_{tj}$ and $G_{rl}$ and the respective phases $\phi_{tj}$ and $\phi_{rl}$ of the inputted desired respiratory signal $R_{tj}(t)$ and real respiratory signal $R_{rl}(t)$ that are synchronized with each other, and that also calculates the gain ratio ($G_{rl}/G_{tj}$) and the phase difference ($\phi_{rl}-\phi_{tj}$); a respiratory state evaluation unit 7cE2 that evaluates a respiratory state, based on the calculated respiration evaluation information; and a navigation modification information generating unit 7cE3 that generates respiratory navigation modification information $I_{md}$, based on a respiratory state evaluation result $I_{ev}$. The modification information $I_{md}$ is outputted to a respiratory induction control unit 7cC and is utilized when there is generated display data to be displayed, for example, on such a display device as illustrated in FIG. 5. In addition, it goes without saying that the respiratory induction apparatus 7 has a function of determining, based on the real respiratory signal and the desired respiratory signal, whether or not particle-beam irradiation onto a patient should be implemented; this function is undertaken by the respiratory induction control unit 7cC.

The navigation modification information generating unit 7cE3 also generates specific instructions for modifying the phase (to be advanced or delayed) and the gain (deep or shallow) of the respiratory signal. For example, when the navigation modification information generating unit 7cE3 determines that the phase is delayed more than anticipated, it generates the modification information $I_{md}$ suggesting that the respiration needs to be advanced. In such a manner as described above, for example, the navigation modification information generating unit 7cE3 generates image data to be displayed, in the message column of FIG. 5, as "please advance your respiration a bit"; concurrently the navigation modification information generating unit 7cE3 generates sound data so as to transmit the same contents by means of sound and controls the respiratory information instruction apparatus 7b. In the case where the gain itself is displayed, the value obtained by adding the gain ratio data to the modification information $I_{md}$ is outputted so that there is displayed the gain value at the time when the gain of the desired respiratory signal is set to be 100. The respiratory induction control unit 7cC generates image data for displaying the outputted value, for example, in numbers or in a graph. As described above, as far as the display method is concerned, the value may either directly be displayed or graphed as a level gauge; the respiratory induction control unit 7cC may perform the display through the method designated by the input through the input I/F.

However, even in the case where as described above, the desired respiratory waveform and the real respiratory waveform are displayed in real time on the same temporal axis, delay in the respiratory of a person is inevitable and hence the real respiratory signal is liable to be desynchronized with the desired respiratory waveform. In this situation, it is assumed that the phase $\phi_{rl}$ of the real respiratory signal, calculated by the respiration evaluation information calculation unit 7cE1, is always delayed by $\theta$ from the phase $\phi_{tj}$ of the desired respiratory signal, i.e., a constant-value ($-\theta$) phase difference is maintained in several periods. In this case, it is conceivable that the reason why the delay is caused is that the method of issuing instructions through the sense of hearing and the sense of eyesight is wrong, i.e., the method is not suited to the characteristics of a patient. In other words, provided the phase of the real respiration is always delayed by θ, the issue of instruction may be advanced by θ. That is to say, in the case where the respiratory state evaluation unit 7cE2 determines that the phase delay or the phase advance is of a constant value, the navigation modification information generating unit 7cE3, in addition to the evaluation result $I_{ev}$, feedbacks the phase delay (advance) of the real respiratory signal to the respiratory navigation computer, and then generates and outputs the modification information $I_{md}$ for advancing the instruction. As a result, it is not required that the patient changes by himself the way of synchronizing his respiration with the desired respiration; therefore, he can readily synchronize his respiration with the desired respiration.

The method of utilizing phase information in the respiratory signal has been explained; however, it goes without saying that utilization of gain information enables a satisfactory effect to be expected. It has been reported that when a person feels sleepy, his respiration tends to be shallow. A respiration gain is nothing but an index for representing the depth (amplitude) of respiration. Accordingly, by comparing the desired respiration with the real respiration, an instruction such as "more deeply" can be issued. In contrast, when the real respiration becomes larger than the desired respiration, the instruction "less deeply" is issued. These instructions, in conjunction with sound, may be displayed in the message column on the display screen in FIG. 5

The foregoing operation will be explained with reference to the flowchart in FIG. 8.

In FIG. 8, when the operation of respiratory navigation is started, at first, the synchronization timing and the period are set based on the timing signal inputted from the control unit 4 and period information, in order to synchronize the respiratory navigation timing with the operation cycle of the accelerator 1 (the step S10). Next, based on the data on the desired respiratory waveform, obtained for the patient, and the set period and synchronization timing, the desired respiratory signal $R_{tj}(t)$ is generated and the desired respiratory waveform is shown (the step S20). When the patient starts respiration in accordance with the desired respiratory waveform, the real respiratory signal $R_{rl}(t)$ is measured (the step S30). From the real respiratory signal $R_{rl}(t)$ and the desired respiratory signal $R_{tj}(t)$, respiration evaluation information including at least the gain G and the phase φ is calculated (the step S40), and based the calculated respiration evaluation information, the respiratory state is evaluated (the step S50); in the case where the ratio of the gain $G_{res}$ and the phase difference Δφ, which are information for evaluating the misalignment between the real respiratory signal and the desired respiratory signal, are within tolerance (the determination result in the step S60 is "Y"), the respiratory navigation is continued as it is.

In the case where the misalignment exceeds the tolerance (the determination result in the step S60 is "N") it is further determined whether or not waveform modification is required (the step S200); for example, in the case where it is determined that the phase of the desired respiratory waveform to be shown needs to be modified (the determination result in the step S200 is "Y"), such as in the case where the phase difference Δφ is a constant value, the timing of showing the waveform is modified by Δφ (the step S230), and shifted to the step S20. In contrast, in the case where it is only necessary to issue an instruction, for example, to enlarge the gain G (the determination result in the step S200 is "N"), the contents for the instruction are generated (the step S210) and the additional instruction is issued (the step S220); then, the respiratory navigation is continued (the step S100). During the respiratory navigation, the determination whether or not irradiation onto a patient should be implemented is continuously implemented based on the real respiratory signal and the desired respiratory signal; however, because this flow is described intensively about the difference between the respiratory navigation and the real respiration, the description about the determination whether or not irradiation should be implemented and the like is omitted.

That is to say, with regard to the inputted real respiratory signal $R_{rl}(t)$ and desired respiratory signal $R_{tj}(t)$ that are synchronized with each other, the respiration evaluation information calculation unit 7cE1 calculates the gain $G_{tj}$ and $G_{rl}$ and the phases $\phi_{tj}$ and $\phi_{rl}$ by mathematically processing the real respiratory signal $R_{rl}(t)$ and desired respiratory signal $R_{tj}(t)$ acquired in synchronization with the period of the desired respiratory signal $R_{tj}(t)$; then, the respiratory state evaluation unit 7cE2 that evaluates the respiratory state, based on the calculated quantitative respiration evaluation information. As a result, it is made possible that by quantitatively evaluating the misalignment of the real respiration from the desired respiration, the timing of respiratory induction is modified or an appropriate instruction is issued so that even though a patient is not conscious, his respiration is modified.

Next, by calculating quantitative information for evaluating the respiratory state, not only the respiratory state but also the physiological state of a patient can be evaluated. Hereinafter, there will be described the evaluation of patient physiological state based on the respiration evaluation information. In general, it is said that a single treatment time in particle beam therapy is from 15 min. to 30 min., and approximately 1 min. to 2 min. out of the treatment time is an irradiation time. The time excluding the irradiation time is utilized for positioning a diseased site and for synchronizing the real respiration with the desired respiration. Naturally, it is possible that during the treatment time, the patient falls into a sleep or has a strong cough. In respiratory induction, it is useful that from the real respiratory waveform of a patient, the sleeping state and the coughing state of the patient can be detected.

In general, in the case where a patient is trying to synchronize his real respiration with the desired respiratory waveform, the gain and the phase of the real respiratory signal tends to gradually come close to the gain and the phase of the desired respiratory signal. However, when the patient falls into a sleep, the gain of the real respiratory signal gradually becomes small, and the phase of the real respiratory signal gradually loses the correlation with the phase of the desired respiratory signal. Thus, the respiratory state evaluation unit 7cE2 is provided with a function of determining that the probability of being in a sleep is high, when the gain $G_{rl}$ of the real respiratory signal $R_{rl}(t)$ becomes lower than a preliminarily set value. In this case, the respiratory state evaluation unit 7cE2 outputs the evaluation result $I_{ev}$ suggesting the probability that the patient has fallen into a sleep, and the navigation modification information generating unit 7cE3 generates the modification information $I_{md}$ for displaying on the display screen a message indicating that the probability of being in a sleep is high or for modifying a display so that there can be outputted a sound output for urging the patient to awake.

In a particle beam therapy system, in many cases, in an irradiation operation room, which is other than the treatment room, a doctor, an engineer, or the like can view a display screen on which there are displayed the same contents as those on another display screen that is viewed by a patient. In this case, when this message is kept viewed, even though being on standby in the irradiation operation room, the doctor, engineer, or the like who views the message can awake the patient by speaking to the patient by means of an interphone or the like.

As described above, the doctor, engineer, or the like who provides medical treatment is on standby in an irradiation operation room separated from the treatment room, in order to avoid exposure to a particle beam. Conversation is available between the treatment room and the irradiation operation room by means of an interphone or the like; in many cases, it is made possible to view or listen to a patient by use of a camera-equipped monitor. Thus, when the patient has a strong cough, the doctor, engineer, or the like can learn it by means of the interphone or the like. In general, in the case where a patient is normally trying to synchronize his respiration with the desired respiratory waveform, the gain and the phase of the real respiratory signal gently change and come close to the gain and the phase of the desired respiratory signal. However, when the patient has a strong cough, the gain and the phase of the real respiratory waveform drastically change. Thus, the respiratory state evaluation unit $7cE2$ is provided with a function of determining that the probability of having a strong cough is high, when the changing rate of the gain $G_{rl}$ or the phase $\phi_{rl}$ of the real respiratory signal $R_{rl}(t)$ exceeds a preliminarily set range. In this case, the respiratory state evaluation unit $7cE2$ outputs the evaluation result suggesting that the probability that the patient has a strong cough is high, and the navigation modification information generating unit $7cE3$ generates the modification information $I_{md}$ for displaying on the display screen a message indicating that the probability that the patient has a strong cough is high.

Even in this case, when in the irradiation operation room separated from the treatment room, this message is kept viewed by the doctor, engineer, or the like who provides medical treatment, even though being on standby in the irradiation operation room, the doctor, engineer, or the like who views the message can relax the patient by speaking to him or her by means of an interphone or the like so as to release the patient from the cough or the doctor, engineer, or the like can let the patient have a temporary rest, in some cases.

In addition, there are other merits in utilizing the gain and the phase obtained through the equations (3) and (4). A real respiratory signal is obtained through measurement by the respiratory sensor; basically, a desired respiratory signal is acquired from a value obtained through measurement by the same sensor. However, in some cases, no matter what kind of sensor is utilized, there exists a difference between the offset at a time when the desired respiratory signal is obtained and the offset at a time when the real respiratory signal is obtained through measurement. The offset denotes the offset term (referred to also as a bias term, a DC component, or 0th-order term) "$a_0/2$. That is to say, it is a constant term that does not depend on the time. For example, in the case where the abdominal movement is measured by a laser displacement gauge, the average distance to the abdomen corresponds to the offset. However, because in the foregoing method, only the 1st-order term in the equation (1) is utilized, the gain and the phase can be obtained regardless of the value of the offset term. For reference's sake, the range (the inner-body position of the Bragg peak) of a particle beam depends on the depth from the body surface. The depth from the body surface is more important than the propagation distance in the air. Accordingly, in the measurement signal obtained by the respiration synchronization sensor, the offset term is not so important; according to this method, not only the measurement of real respiratory can be started without implementing offset adjustment for the respiration synchronization sensor, but also the real respiratory state can be evaluated.

As described above, the respiratory induction apparatus $7$ according to Embodiment 1 is to induce the respiration of a patient in particle beam therapy; the respiratory induction apparatus $7$ is configured in such a way as to include the respiratory induction control unit $7cC$ that functions as a desired respiratory signal generating unit that generates the desired respiratory signal $R_{tj}(t)$ for inducing the respiration of a patient; the real respiration measurement unit $7a$ that measures the real respiration of a patient and outputs the real respiratory signal $R_{rl}(t)$ obtained through the measurement; and the respiration evaluation unit $7cE$ in which by, as a calculation unit, utilizing data of a single period $T_{res}$ of the desired respiratory signal $R_{tj}(t)$, there is calculated a pair of coefficients $a_1$ and $b_1$, of trigonometric functions, which correspond to the 1st-order terms by means of Fourier series expansion of data of the desired respiratory signal $R_{tj}(t)$ and data of the real respiratory signal $R_{rl}(t)$, which is acquired in synchronization with the data of the desired respiratory signal $R_{tj}(t)$, and there are performed comparisons between the gain $G_{tj}$ with the gain $G_{rl}$ and between the phase $\phi_{tj}$ with the phase $\phi_{rl}$, which are obtained from the calculated coefficients $a_1$ and $b_1$, respectively, so that there is evaluated a misalignment of the real respiration (strictly speaking, the real respiratory signal $R_{rl}(t)$, which is the measurement value of the real respiration) from the desired respiratory signal $R_{tj}(t)$. Therefore, by accurately evaluating the respiration, the respiration can appropriately be induced. Moreover, even though there exists a difference between the offset at a time when real respiration is measured in obtaining the desired respiratory waveform and the offset at a time when real respiration is measured during treatment, the difference does not affect the evaluation result; therefore, treatment can be implemented even without carrying out offset adjustment.

Still moreover, the respiration evaluation unit $7cE$ determines the state of real respiration, based on the changing rate of the compared difference $\Delta\phi$ between the phase $\phi_{tj}$ of the desired respiratory signal and the phase $\phi_{rl}$ of the real respiratory signal and/or the changing rate of the compared ratio of the gain $G_{rl}$ of the real respiratory signal to the gain $G_{tj}$ of the desired respiratory signal $R_{tj}(t)$; therefore, even the physiological state of a patient such as being in a sleep or having a strong cough can also be grasped.

In particular, when determining that the phase difference $\Delta\phi$ has maintained a constant value for a predetermined time, the respiration evaluation unit $7cE$ generates the modification information $I_{md}$ for modifying the phase of the desired respiratory signal shown during the navigation, and the respiratory induction control unit $7cC$, which is a desired respiratory signal generating unit, generates the desired respiratory signal whose phase is shifted by a given value, based on the modification information $I_{md}$; therefore, even though the patient is unconscious, the real respiration can naturally be synchronized with the desired respiration.

Furthermore, the particle beam therapy system according to Embodiment 1 includes the accelerator $1$ that generates a particle beam; a plurality of treatment rooms $6$; the particle beam transport path $3$ that connects the accelerator $1$ with each of the plurality of treatment rooms $6$; the switching electromagnet $32$, provided in the transport path $3$, that is a switching device for switching the orbits of a particle beam generated by the accelerator $1$, in such a way that the particle beam is supplied to one of the plurality of treatment rooms $6$; the foregoing respiratory induction apparatus $7$ provided in each of the plurality of treatment rooms $6$; and the irradiation apparatus $21$, provided in each of the plurality of treatment rooms 6, that forms a supplied particle beam into an irradiation field corresponding to an irradiation subject and controls irradiation onto the irradiation subject, in synchronization with at least the desired respiratory signal $R_{tj}(t)$. Therefore, by accurately evaluating the respiration, the respiration can appropriately be induced, whereby accurate irradiation can be performed.

Still moreover, the desired respiratory signal generating unit 7cC generates the desired respiratory signal $R_{tj}(t)$ in synchronization with the operation of the accelerator 1; therefore, the respiration can accurately be synchronized with the characteristics of the accelerator, whereby accurate and efficient irradiation can be performed.

The switching device 32 switches the orbits of a particle beam, based on the information $I_{ev}$ on the misalignment of the real respiration from the desired respiratory signal evaluated by the respiration evaluation unit 7cE in each of the plurality of treatment rooms 6; therefore, it is made possible to provide medical treatment while selecting the treatment room where accurate irradiation can be performed during the present time.

Embodiment 2

It goes without saying that in the respiratory induction apparatus 7 according to Embodiment 1, the respective portions, represented in the block diagram of FIG. 6, for performing, for example, the operation represented in FIG. 8 can be configured by use of dedicated hardware. However, it can be understood that the functions of the portions, in the respiratory induction apparatus 7, other than the respiration synchronization sensor 7a among the portions illustrated in FIG. 6 can be realized by a universal computer or a workstation. That is to say, in the case where it is assumed that a universal computer or a workstation is utilized, most of the functions in respiratory navigation can readily be realized by use of a program that works on the computer or the like. Accordingly, in Embodiment 2, there will be explained a program for realizing a respiratory induction apparatus on a computer. In Embodiment 2, this program is referred to as a "respiratory induction program according to an embodiment of the present invention". In some cases, the display, the speaker, and the like are, in practice, customized so that a lying patient can easily view them; however, with regard to the function of displaying, they are the same as the displays and the like belonging to an ordinary computer; thus, the explanation herein will be made under the assumption that a respiratory induction apparatus excluding the respiration synchronization sensor 7a can be realized by installing the program in the computer.

A large-size complicated program is divided into modules, which are functional units, so as to be designed and developed. In Embodiment 2, the respiratory induction program is divided into modules (basic modules) that are general and essential for the respiratory induction program and modules (additional modules) that are added for the respiratory induction program according to an embodiment of the present invention, and then explanation therefor will be made with reference to the module block diagram in FIG. 9 including the corresponding blocks explained in Embodiment 1.

Figure 9:
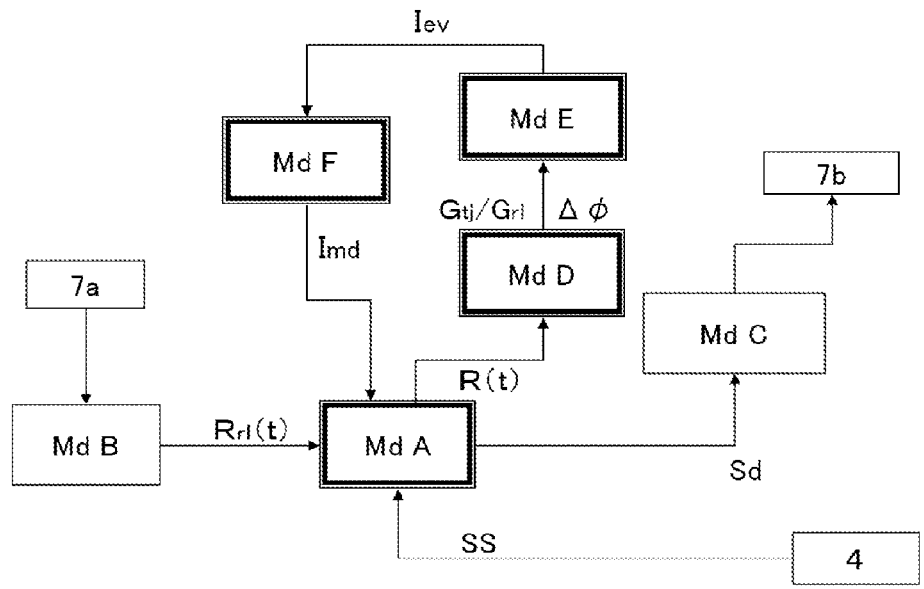
FIG. 9 is a block diagram for explaining the configuration of a respiratory induction program installed in a computer for the purpose of realizing a respiratory induction apparatus according to Embodiment 2 of the present invention.

As the basic modules, a module A (corresponding to 7cC) for controlling the whole operation of respiratory navigation, especially, for synchronization-controlling the modules (described as "Md" in FIG. 9), a module C (corresponding to 7cC) for creating display data Sd in order to display on the display screen the desired respiratory signal $R_{tj}(t)$ outputted from the module A and for performing sound guidance, and a module (corresponding to 7cI/O) for receiving the real respiratory signal $R_{rl}(t)$ measured by the respiration synchronization sensor 7a are essential. With regard to the module C, it is desirable that in order to make a patient aware of the respiratory difference, there is further provided a function of creating the display data Sd for displaying, on the display screen, the real respiratory signal $R_{rl}(t)$ on the same temporal axis as the desired respiratory signal $R_{tj}(t)$ is displayed. In FIG. 9, the module A undertakes the function of determining based on the real respiratory signal $R_{rl}(t)$ and the desired respiratory signal $R_{tj}(t)$ whether or not particle-beam irradiation onto a patient should be implemented and creating a gate signal.

As the additional modules, there are provided a module D (corresponding to 7cE1) for calculating the gain G and the phase φ, which are respiration evaluation information for evaluating the respiratory state, from the respiratory signal R(t) (the desired respiratory signal Rtj(t) and the real respiratory signal Rrl(t)); a module E (corresponding to 7cE2) for evaluating the respiratory state from the calculated gain G and phase φ of the respiratory signal so as to generate the evaluation result $I_{ev}$, which is useful information for navigating the respiration; and a module F (corresponding to 7cE3) that generates, based on the evaluation result $I_{ev}$, the respiratory navigation modification information $I_{md}$ and for modifying the respiratory navigation. Additionally, it goes without saying that by adding these additional modules, the configurations of the basic modules are appropriately modified.

In this embodiment, the "useful information for navigating the respiration" denotes, for example, the following items. In the case where the gain of the real respiratory signal is $G_{rl}$, the value at a time when the gain $G_{tj}$ of the desired respiratory signal is set to 100 is the evaluation result $I_{ev}$ and also becomes the modification information $I_{md}$, which is information to be displayed with a level gauge or the like on the display screen. In the case where the phase of the real respiratory signal is $\phi_{rl}$, the information obtained by visualizing the phase advance or the phase delay from the phase $\phi_{tj}$ of the desired respiratory signal is displayed on the display screen. Furthermore, there is also included determination information at a time when these values are compared with predetermined values. Similarly, there is also included determination information as to whether or not the changing rate of the gain or the phase exceeds a predetermined value. The useful information includes the items to be displayed on the display screen and the method therefor and the items to be instructed by the sound-or-the-like instruction unit and the method therefor, which are explained in each of the embodiments, described later.

The operation of the respiratory induction program provided with the foregoing modules will be explained while taking into account the relationship with the steps in the flowchart in FIG. 8 utilized in the explanation of Embodiment 1.

The module A sets the synchronization timing and the period, based on a timing signal SS inputted from the control unit 4 and period information, in order to synchronize the respiratory navigation timing with the operation cycle of the accelerator 1 (the step S10). Next, based on the data on the desired respiratory waveform, obtained for the patient, and the set period and synchronization timing, the module A generates the desired respiratory signal $R_{tj}(t)$, and then the module C shows the desired respiratory waveform (the step S20). When the patient starts respiration in accordance with the desired respiratory waveform, the module B measures the real respiratory signal $R_{rl}(t)$ (the step S30).

Then, from the real respiratory signal $R_{rl}(t)$ and the desired respiratory signal $R_{tj}(t)$, a module D calculates respiration evaluation information including at least the gain G and the phase φ (the step S40: repeated continuously). A module E evaluates the respiratory state, based on the calculated respiration evaluation information, and outputs the evaluation result $I_{ev}$ (the step S50); in the case where the misalignment between the real respiratory signal and the desired respiratory signal is within a tolerance (the determination result in the step S60 is "Y"), a module F generates the modification information $I_{md}$ for continuing the navigation as it is. In the case where the misalignment exceeds the tolerance (the determination result in the step S60 is "N"), the module F further determines whether or not waveform modification is required (the step S200); for example, in the case where it is determined that the phase of the desired respiratory waveform to be shown needs to be modified (the determination result in the step S200 is "Y"), such as in the case where the phase difference $\Delta\phi$ is a constant value, the module F generates the modification information $I_{md}$ for correcting the waveform showing timing by $\Delta\phi$ (the step S230), and shifts to the step S20. In contrast, in the case where it is only necessary to issue an instruction, for example, to enlarge the gain G (the determination result in the step S200 is "N"), the module F generates the modification information $I_{md}$ for showing the instruction (the step S210). Then, the module A instructs the module C to generate the display data Sd for performing the modified indication (the step S220) and continues the navigation (the step S100). During the respiratory navigation, the module A continuously performs the determination whether or not irradiation onto a patient should be implemented based on the real respiratory signal $R_{rl}(t)$ and the desired respiratory signal $R_{tj}(t)$.

As described above, the respiratory induction program according to Embodiment 2 is to establish a respiratory induction apparatus that induces the respiration of a patient in particle beam therapy; the respiratory induction program is configured in such a way as to include the desired respiratory signal generating step S20 in which there is generated the desired respiratory signal $R_{tj}(t)$ for inducing the respiration of a patient; the real respiratory measurement step S30 in which the real respiration of a patient is measured and the real respiratory signal $R_{rl}(t)$ obtained through the measurement is outputted; and the respiration evaluation steps S40 through S220 in which by, as a calculation unit, utilizing data of a single period $T_{res}$ of the desired respiratory signal $R_{tj}(t)$, there is calculated a pair of coefficients $a_1$ and $b_1$, of trigonometric functions, which correspond to the 1st-order terms by means of Fourier series expansion of data of the desired respiratory signal $R_{tj}(t)$ and data of the real respiratory signal $R_{rl}(t)$, which is acquired in synchronization with the data of the desired respiratory signal $R_{tj}(t)$, and there are performed comparisons between the gain $G_{tj}$ with the gain $G_{rl}$ and between the phase $\phi_{tj}$ with the phase $\phi_{rl}$, which are obtained from the calculated coefficients $a_1$ and $b_1$, respectively, so that there is evaluated the misalignment between the real respiration (strictly speaking, the real respiratory signal $R_{rl}(t)$, which is the measurement value of the real respiration) and the desired respiratory signal $R_{tj}(t)$. Therefore, by accurately evaluating the respiration, the respiration can appropriately be induced; moreover, even though there exists a difference between the offset at a time when real respiration is measured in obtaining the desired respiratory waveform and the offset at a time when real respiration is measured during treatment, the difference does not affect the evaluation result; therefore, on a computer, there can be established a respiratory induction apparatus with which treatment can be implemented even without carrying out offset adjustment.

Embodiment 3

In Embodiment 3 of the present invention, in the quantitative evaluation of respiration, there is implemented a comprehensive evaluation in addition to the evaluation of the gain and the phase, described in Embodiments 1 and 2. The method in which real respiration is most directly evaluated is a method of evaluating the error between the real respiratory signal $R_{rl}(t)$ and the desired respiratory signal $R_{tj}(t)$ as represented in the equation (5).

$$J_{res} := \int_0^{2\pi} (R_{rl}(t) - R_{tj}(t))^2 \, d\omega_{res} t \tag{5}$$

where $J_{res}$ is an evaluation function.

In the equation (5), the evaluation function $J_{res}$ is given as a function of continuous time; however, as explained in the "calculation performed every sampling period" of Embodiment 1, $J_{res}$ is discretely calculated in practice. As is the case with the equation (2), the integration range of the equation (5) for calculating the evaluation function $J_{res}$ is a single respiration period $T_{res}$. Accordingly, as is the case with the equation (2), it is conceivable that with regard to the frequency of the calculation, there exist roughly two methods, i.e., every respiratory period or every sampling period. However, in this evaluation, the gain and the phase can be calculated independently; therefore, as long as the respective signals to be utilized for the calculation can be acquired (synchronized) in the same time zone, it is not necessarily required to synchronize the acquisition timing with the calculation in the equation (2).

Figure 10:
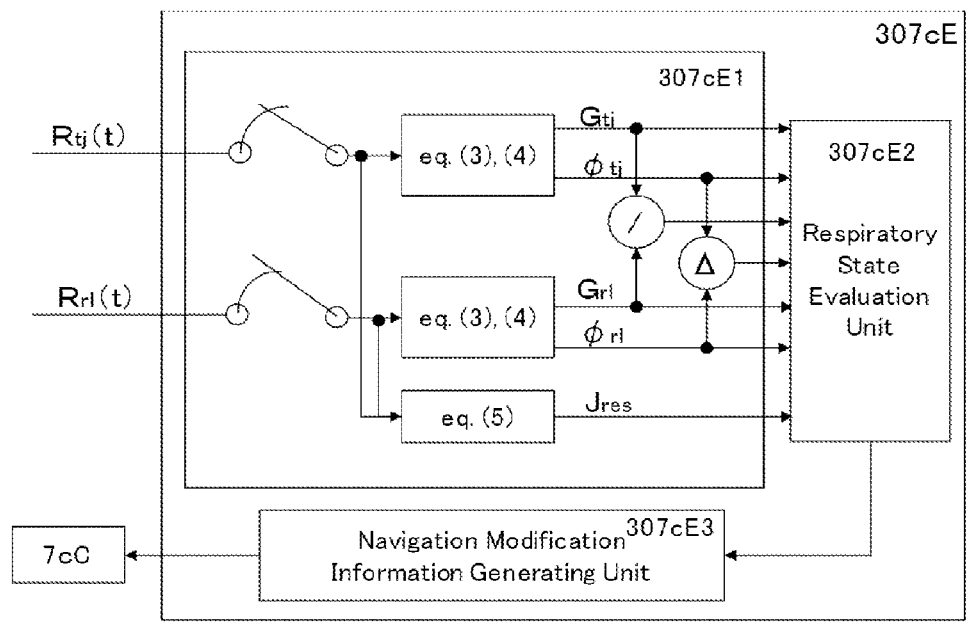
FIG. 10 is a block diagram for explaining the configuration of a respiration evaluation unit of a respiratory induction apparatus according to Embodiment 3 of the present invention.
Figure 11:
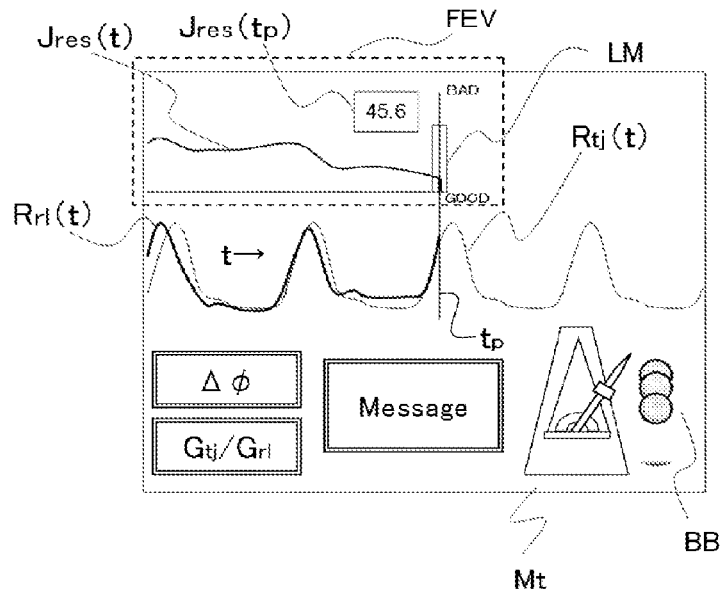
FIG. 11 is a chart representing an example of display screen displayed when respiration is induced in the respiratory information instruction apparatus of a respiratory induction apparatus according to Embodiment 3 of the present invention.

In order to implement the calculation according to the equation (5), a respiratory induction apparatus according to Embodiment 3 is, as represented in FIG. 10, provided with an evaluation function calculation function unit in a respiration evaluation unit 307cE. With regard to the result $J_{res}$, as illustrated in FIG. 11, for example, by providing a display window FEV, the serial data $J_{res}(t)$ may be represented with a graph, as a history from the past; alternatively, the present value $J_{res}(t_p)$ may be indicated by numerals or by a level meter LM. As a result, the patient, the doctor, and the like can numerically or intuitively realize how comprehensively the real respiration coincides with the desired respiratory waveform.

As described above, a respiratory induction apparatus 307 according to Embodiment 3 and the particle beam therapy system provided with the respiratory induction apparatus 307 are configured in such a way that the respiration evaluation unit 307cE calculates the error $J_{res}$ between the desired respiratory signal $R_{tj}(t)$ and the real respiratory signal $R_{rl}(t)$ in a predetermined time, and evaluates the misalignment of the real respiration from the desired respiratory signal $R_{tj}(t)$, including the calculated error $J_{res}$ between the signal data items; therefore, the amount of the real-respiratory difference can comprehensively be evaluated, whereby the effectiveness of a treatment and the appropriateness of a dose distribution can further be raised. For example, as an effect for a patient, there can be given, as a numeral value, the level how the real respiration has come close to the desired respiration. As an effect for the doctor, the engineer, and the like, the circumstances whether or not irradiation of a particle beam is possible can quantitatively be recognized with a single numeral. In other words, there can more efficiently be realized irradiation in which the effect of organ movement caused by the respiration of a patient is eliminated.

Embodiment 4

In Embodiment 3, in addition to the evaluation method utilizing the gain and the phase, there has been described the method in which evaluation is made based on how close to the desired respiration the real respiration is. The closer to the desired respiration, which is the ground for a treatment plan, the real respiration is, the more ideal the circumstances are.

However, it is not necessarily required to make the respiratory waveforms completely the same as each other. Accordingly, in Embodiment 4, as a comprehensive evaluation method added to the evaluation method utilizing the gain and the phase, there will be explained a method in which the condition is relaxed compared with the condition in Embodiment 3 so that respiration is comprehensively evaluated.

In this Embodiment, in the evaluation, there is utilized a respiration gate signal for performing control as to whether or not particle-beam irradiation onto a patient should be implemented is implemented based on the real respiratory signal and the desired respiratory signal. For the clarity of explanation, the "respiration gate signal" will be defined. The explanation will be made with reference to FIG. 3 that has been utilized in the explanation of Embodiment 1. FIG. 3 represents that out of respiratory signals, the desired respiratory signal $R_{tj}(t)$ is approximated by the describing function $D_1(t)$; because the same also applies to the real respiratory signal $R_{rj}(t)$, the explanation will be made while reading the desired respiratory signal $R_{tj}(t)$ as a common respiratory signal $R(t)$. In FIG. 3, the abscissa is the time axis; the more rightward the coordinates move, the more in the future the time advances. The ordinate in the upper column of FIG. 3 denotes the respiratory state; the upward movement means the state of "inspiration", and the downward movement means the state of "expiration". In general, it is known that the organs of a patient are stabilized when the respiration is in the "expiration" state. Accordingly, in particle beam therapy, both the treatment plan and the actual treatment are set under the condition that irradiation is implemented when the respiration of a patient is in the state of "expiration". For that purpose, a threshold value L is set with respect to the respiratory signal $R(t)$, and it is determined whether or not the respiratory signal $R(t)$ is smaller than the threshold value L. As a signal that indicates whether or not the respiratory signal $R(t)$ is smaller than the threshold value L, a respiration gate signal $P(t)$ is utilized.

In this situation, defining that the respiration gate signal $P(t)$ becomes ON when the respiratory signal $R(t)$ is smaller than the preliminarily set threshold value L, and in other cases, the respiration gate signal $P(t)$ becomes OFF. The respiration gate signal $P(t)$ is represented as the equation (6) and, as a value, takes two values (1 bit).

$$P(t) = \begin{cases} 1 & \text{if } P(t) < L \\ 0 & \text{if } P(t) \geq L \end{cases} \quad (6)$$

Here, the respiration gate signal produced for the desired respiratory signal $R_{tj}(t)$ is represented by $P_{tj}(t)$ and the respiration gate signal produced for the real respiratory signal $R_{rj}(t)$ is represented by $P_{rj}(t)$ so that the respiration gate signals are distinguished from each other.

In Embodiment 4, by utilizing the respiration gate signal $P(t)$ defined as described above, comprehensive evaluation of respiration is performed. Specifically, as the error between the respective respiration gate signals $P_{rj}(t)$ and $P_{tj}(t)$ that are produced based on the desired respiratory signal and the real respiratory signal, an evaluation function $J_{res2}$ represented in the equation (7) is calculated, so that the evaluation is performed.

$$J_{res2} := \int_0^{2\pi} (P_{rj}(t) - P_{tj}(t))^2 \, d\omega_{res} t \quad (7)$$

In the equation (7), the evaluation function $J_{res2}$ is given as a function of continuous time; however, as explained in Embodiment 3, $J_{res2}$ is also calculated discretely. As is the case with the equation (2), the integration range of the equation (7) for calculating the evaluation function $J_{res2}$ is a single respiration period $T_{res}$. Accordingly, as is the case with the equation (2), it is conceivable that with regard to the frequency of the calculation, there exist roughly two methods, i.e., every respiratory period or every sampling period. However, in this evaluation, the gain and the phase can be calculated independently; therefore, as long as the respective signals to be utilized for the calculation can be acquired (synchronized) in the same time zone, it is not necessarily required to synchronize the acquisition timing with the calculation in the equation (2).

Figure 12:
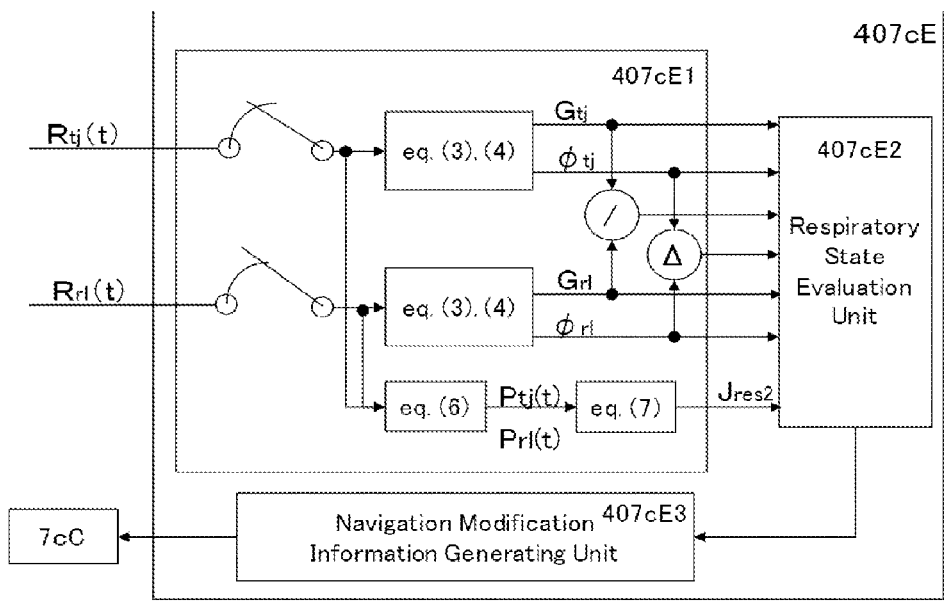
FIG. 12 is a block diagram for explaining the configuration of a respiration evaluation unit of a respiratory induction apparatus according to Embodiment 4 of the present invention.

In order to implement the calculation according to the equation (7), a respiratory induction apparatus according to Embodiment 4 is, as represented in FIG. 12, provided with an evaluation function calculation function unit in a respiration evaluation unit 407cE. As explained in Embodiment 3, the calculation result $J_{res2}$ may also be displayed to the patient by means of the respiratory induction apparatus. Additionally, in FIG. 12, it is described that a respiration evaluation information calculation unit 407cE1 undertakes the function of calculating the respiration gate signal $P(t)$ from the respiratory signal $R(t)$, based on the equation (6); however, the respiration gate signal $P(t)$ calculated by the respiratory induction control unit 7cC may be utilized.

As described above, a respiratory induction apparatus 407 according to Embodiment 4 and the particle beam therapy system provided with the respiratory induction apparatus 407 are configured in such a way that there is provided the respiration evaluation unit 407cE or a respiratory induction control unit that functions as a respiration gate signal transformation unit for transforming the desired respiratory signal $R_{tj}(t)$ and the real respiratory signal $R_{rj}(t)$ into the respiration gate signals $P_{rj}(t)$ and $P_{tj}(t)$, respectively, suggesting whether or not the desired respiratory signal $R_{tj}(t)$ and the real respiratory signal $R_{rj}(t)$ are smaller than a predetermined threshold value, and in such a way that the respiration evaluation unit 407cE calculates the error $J_{res2}$ between the respiration gate signals $P_{rj}(t)$ and $P_{tj}(t)$ obtained through the transformation, and evaluates the misalignment of the real respiration from the desired respiratory signal $R_{tj}(t)$, including the calculated error $J_{res2}$; therefore, by weighting the "expiration" state, of respiration, that is required for the actual treatment, the amount of the real-respiratory difference can comprehensively be evaluated, whereby the effectiveness of a treatment and the appropriateness of a dose distribution can further be raised. Moreover, because the respiration gate signal utilized for irradiation control can be utilized and is simplified to two values, calculation processing can readily be performed.

Embodiment 5

In Embodiment 4, as a method of comprehensively evaluating respiration, there has been described a method in which by utilizing the respiration gate signal $P(t)$, the timing of expiration is emphasized. In Embodiment 5, there will be described a method in which by utilizing a describing function, information on the gain and the phase of respiration is emphasized.

With regard to a describing function, in Embodiment 1, there has been explained 1st-order term $D_1(t)$ by means of Fourier series expansion of the data corresponding to a single period of the respiratory signal R(t); however, in Embodiment 5, there are utilized a describing function $D_2(t)$ defined by the equation (8) by utilizing the gain $G_{res}$ and the phase $\phi_{res}$ calculated from $D_1(t)$.

$$D_2(t) = G_{res} \cos(\omega_{res} t + \phi_{res}) \quad (8)$$

Here, the describing function produced for the desired respiratory signal $R_{tj}(t)$ is represented by $D_{2tj}(t)$ and the describing function produced for the real respiratory signal $R_{rl}(t)$ is represented by $D_{2rl}(t)$ so that the describing functions are distinguished from each other.

There will be explained a method in which by utilizing the describing function $D_2(t)$ defined as described above, the evaluation of respiration is performed. Specifically, as the error between the respective describing functions $D_{2tj}(t)$ and $D_{2rl}(t)$ that are produced based on the desired respiratory signal and the real respiratory signal, respectively, an evaluation function $J_{res3}$ represented in the equation (9) is calculated, so that the evaluation is performed.

$$J_{res3} := \int_0^{2\pi} (D_{rl}(t) - D_{tj}(t))^2 \, d\omega_{res} t \quad (9)$$

In the equation (9), the evaluation function $J_{res3}$ is given as a function of continuous time; however, as explained in Embodiment 3, $J_{res3}$ is also calculated discretely. As is the case with the equation (2), the integration range of the equation (9) for calculating the evaluation function $J_{res3}$ is a single respiration period $T_{res}$. Accordingly, as is the case with the equation (2), it is conceivable that with regard to the frequency of the calculation, there exist roughly two methods, i.e., every respiratory period or every sampling period.

Figure 13:
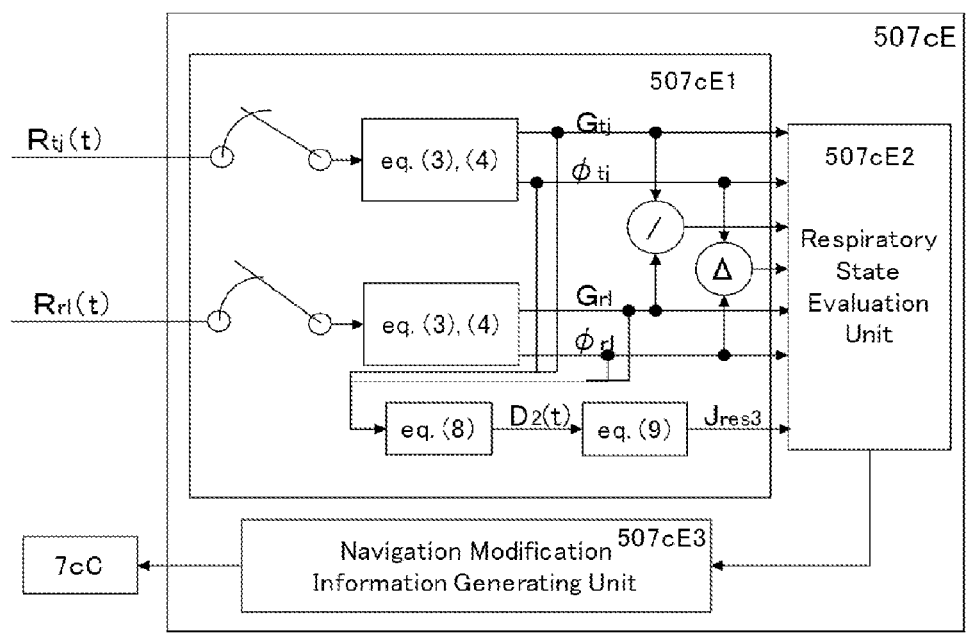
FIG. 13 is a block diagram for explaining the configuration of a respiration evaluation unit of a respiratory induction apparatus according to Embodiment 5 of the present invention.

In order to implement the definition of the describing function $D_2(t)$ according to the equation (8) and the calculation according to the equation (9), a respiratory induction apparatus according to Embodiment 5 is, as represented in FIG. 13, provided with a describing function defining function unit and an evaluation function calculation function unit in a respiration evaluation unit 507cE. As explained in Embodiments 3 and 4, the calculation result $J_{res3}$ may also be displayed to the patient by means of the respiratory induction apparatus.

As described above, a respiratory induction apparatus 507 according to Embodiment 5 and the particle beam therapy system provided with the respiratory induction apparatus 507 are configured in such a way that the respiration evaluation unit 507cE defines the respective trigonometric functions $(D_2(t) = G_{res} \cos(\omega_{res} t + \phi_{res}))$ by utilizing the respective gains $G_{tj}$ and $G_{rl}$ and the respective phases $\phi_{tj}$ and $\phi_{rl}$ calculated from the desired respiratory signal $R_{tj}(t)$ and the real respiratory signal $R_{rl}(t)$, calculates the error Jres3 between the respective trigonometric functions $D_{2rl}(t)$ and $D_{2tj}(t)$ and evaluates the misalignment of the real respiration from the desired respiratory signal $R_{tj}(t)$, including the calculated error $J_{res3}$; therefore, by weighting the gain and the phase, which represent the state of a respiratory waveform, the amount of the real-respiratory difference can comprehensively be evaluated, whereby the effectiveness of a treatment and the appropriateness of a dose distribution can further be raised.

In each of Embodiments 1 through 5, there has been explained the method in which in each treatment room, irradiation control and modification of the navigation timing are performed based on respiration evaluation information. However, it is not necessarily required that in each treatment room, irradiation control or modification of the navigation timing is performed; for example, they may collectively be performed in a common control unit (4 in FIG. 1) in the particle beam therapy system. Furthermore, the respiration evaluation itself may collectively be performed in the common control unit in the particle beam therapy system, as long as signal processing can be implemented in such a way that no timing difference is caused. In this case, the signal system may be configured in such a way that the respiratory signal obtained through measurement in each treatment room and the respiration evaluation information, the synchronization signal, and the like evaluated therein are exchanged between the control unit and each treatment room. By making a common control unit perform the calculation and the like in such a way as described above, it is not necessary to provide a plurality of apparatuses that perform complicated calculations. Moreover, for example, in the case where treatments are implemented in the same time zone in a plurality of treatment rooms, there can be performed control in which the respective evaluation results in the plurality of treatment rooms are compared with one another, and as a treatment subject, there is selected the treatment room where the respiratory state is most satisfactory (the misalignment between the real respiration and the desired respiration is small). In this case, the control unit controls the course switching deflection electromagnet in such a way that a particle beam is led to the selected treatment room. Alternatively, for example, the respiratory induction can readily be performed in a plurality of treatment rooms in a synchronized manner.

In other words, the switching device 32 switches the orbits of a particle beam, based on the information $I_{ev}$ on the misalignment of the real respiration from the desired respiratory signal evaluated by the respiration evaluation unit 7cE in each of the plurality of treatment rooms 6; therefore, it is made possible to provide medical treatment while selecting the treatment room where accurate irradiation can be performed during the present time.

DESCRIPTION OF REFERENCE NUMERALS

1: accelerator (synchrotron)
2: irradiation system (21: irradiation apparatus, 7: respiratory induction apparatus)
3: transport system (31: transport path, 32: switching electromagnet (switching device))
4: control system (controller) (40: main controller)
6: treatment room
7a: respiration measurement apparatus (respiration synchronization sensor)
7b: respiratory induction instruction apparatus
7c: respiratory induction apparatus main body (7cC: respiratory induction apparatus control unit (desired respiratory signal generating unit, respiration gate signal transformation unit), 7cE: respiration evaluation unit (respiration gate signal transformation unit), 7cI/O: input/output unit), (22a: respiration measurement apparatus))
7d: input/output I/F
$J_{res}$: error
$G_{res}$: gain
P(t): respiration gate signal
R(t): respiratory signal
$T_{res}$: respiration period
$\phi_{res}$: phase Three-digit numbers each denote variant examples in Embodiments.

The invention claimed is:
1. A respiratory induction apparatus for inducing respiration of a patient in particle beam therapy, comprising:

a desired respiratory signal generating unit that generates a desired respiratory signal for inducing respiration of the patient;

a real respiration measurement unit that measures real respiration of the patient and outputs a real respiratory signal obtained through the measurement;

a respiration evaluation unit in which by, as a calculation unit, utilizing data of a single period of the desired respiratory signal, there is calculated a pair of coefficients, of trigonometric functions, which correspond to the 1st-order terms by means of Fourier series expansion of the desired respiratory signal and the real respiratory signal, which is acquired in synchronization with the desired respiratory signal, and there are performed comparisons between the respective gains and between the respective phases, which are obtained from the calculated coefficients, so that there is evaluated a misalignment of the real respiration from the desired respiratory signal; and a modification information generating unit that generates modification information to modify the misalignment of the real respiration, based on the evaluation results by the respiration evaluation unit.

2. The respiratory induction apparatus according to claim 1, wherein the respiration evaluation unit determines the state of the real respiration, based on the changing rate of a difference between the respective phases of the desired respiratory signal and the real respiratory signal and/or changing rate of ratio between the respective gains of real respiratory signal and desired respiratory signal.

3. A particle beam therapy system comprising:
an accelerator that generates a particle beam;
a plurality of treatment rooms;
a particle beam transport path that connects the accelerator with each of the plurality of treatment rooms;
a switching device, provided in the transport path, that switches orbits of a particle beam generated by the accelerator, in such a way that the particle beam is supplied to one of the plurality of treatment rooms;
a respiratory induction apparatus, provided in each of the plurality of treatment rooms, according to claim 2; and
an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

4. The particle beam therapy system according to claim 3, wherein the switching device switches the orbits of a particle beam, based on the misalignment of the real respiration from the desired respiratory signal, evaluated by the respiration evaluation unit in each of the plurality of treatment rooms.

5. The respiratory induction apparatus according to claim 1, wherein when the respiration evaluation unit determines that a difference between the respective phases of desired respiratory signal and real respiratory signal has maintained a constant value for a predetermined time, the modification information generating unit generates the modification information so that the desired respiratory signal generating unit generates a desired respiratory signal whose phase is shifted by the constant value.

6. A particle beam therapy system comprising:
an accelerator that generates a particle beam;
a plurality of treatment rooms;
a particle beam transport path that connects the accelerator with each of the plurality of treatment rooms;
a switching device, provided in the transport path, that switches orbits of a particle beam generated by the accelerator, in such a way that the particle beam is supplied to one of the plurality of treatment rooms;
a respiratory induction apparatus, provided in each of the plurality of treatment rooms, according to claim 5; and
an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

7. The particle beam therapy system according to claim 6, wherein the switching device switches the orbits of a particle beam, based on the misalignment of the real respiration from the desired respiratory signal, evaluated by the respiration evaluation unit in each of the plurality of treatment rooms.

8. The respiratory induction apparatus according to claim 1, wherein the respiration evaluation unit calculates an error between the desired respiratory signal and the real respiratory signal in a predetermined time, and evaluates the misalignment of the real respiration from the desired respiratory signal, including the calculated error.

9. A particle beam therapy system comprising:
an accelerator that generates a particle beam;
a plurality of treatment rooms;
a particle beam transport path that connects the accelerator with each of the plurality of treatment rooms;
a switching device, provided in the transport path, that switches orbits of a particle beam generated by the accelerator, in such a way that the particle beam is supplied to one of the plurality of treatment rooms;
a respiratory induction apparatus, provided in each of the plurality of treatment rooms, according to claim 8; and
an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

10. The particle beam therapy system according to claim 9, wherein the switching device switches the orbits of a particle beam, based on the misalignment of the real respiration from the desired respiratory signal, evaluated by the respiration evaluation unit in each of the plurality of treatment rooms.

11. The respiratory induction apparatus according to claim 1, further including a respiration gate signal transformation unit for transforming the desired respiratory signal and the real respiratory signal into respective respiration gate signals suggesting whether or not the desired respiratory signal and the real respiratory signal are smaller than a predetermined threshold value, wherein the respiration evaluation unit calculates an error between the respective respiration gate signals obtained through the transformation, and evaluates the misalignment of the real respiration from the desired respiratory signal, including the calculated error.

12. A particle beam therapy system comprising:
an accelerator that generates a particle beam;
a plurality of treatment rooms;
a particle beam transport path that connects the accelerator with each of the plurality of treatment rooms;
a switching device, provided in the transport path, that switches orbits of a particle beam generated by the accelerator, in such a way that the particle beam is supplied to one of the plurality of treatment rooms;
a respiratory induction apparatus, provided in each of the plurality of treatment rooms, according to claim 11; and an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

13. The particle beam therapy system according to claim 12, wherein the switching device switches the orbits of a particle beam, based on the misalignment of the real respiration from the desired respiratory signal, evaluated by the respiration evaluation unit in each of the plurality of treatment rooms.

14. The respiratory induction apparatus according to claim 1, wherein the respiration evaluation unit defines respective trigonometric functions by utilizing the respective gains and the respective phases calculated from the desired respiratory signal and the real respiratory signal, calculates an error between the respective defined trigonometric functions, and evaluates the misalignment of the real respiration from the desired respiratory signal, including the calculated error.

15. A particle beam therapy system comprising:
an accelerator that generates a particle beam;
a plurality of treatment rooms;
a particle beam transport path that connects the accelerator with each of the plurality of treatment rooms;
a switching device, provided in the transport path, that switches orbits of a particle beam generated by the accelerator, in such a way that the particle beam is supplied to one of the plurality of treatment rooms;
a respiratory induction apparatus, provided in each of the plurality of treatment rooms, according to claim 14; and
an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

16. The particle beam therapy system according to claim 15, wherein the switching device switches the orbits of a particle beam, based on the misalignment of the real respiration from the desired respiratory signal, evaluated by the respiration evaluation unit in each of the plurality of treatment rooms.

17. A particle beam therapy system comprising:
an accelerator that generates a particle beam;
a plurality of treatment rooms;
a particle beam transport path that connects the accelerator with each of the plurality of treatment rooms;
a switching device, provided in the transport path, that switches orbits of a particle beam generated by the accelerator, in such a way that the particle beam is supplied to one of the plurality of treatment rooms;
a respiratory induction apparatus, provided in each of the plurality of treatment rooms, according to claim 1; and
an irradiation apparatus, provided in each of the plurality of treatment rooms, that forms a supplied particle beam into an irradiation field corresponding to an irradiation subject and controls irradiation onto the irradiation subject, in synchronization with at least the desired respiratory signal.

18. The particle beam therapy system according to claim 17, wherein the desired respiratory signal generating unit generates the desired respiratory signal, in synchronization with the operation of the accelerator.

19. The particle beam therapy system according to claim 17, wherein the switching device switches the orbits of a particle beam, based on the misalignment of the real respiration from the desired respiratory signal, evaluated by the respiration evaluation unit in each of the plurality of treatment rooms.

20. A respiratory induction program for establishing on a computer a respiratory induction apparatus that induces respiration of a patient in particle beam therapy, the respiratory induction program comprising:
a desired respiratory signal generating step in which there is generated a desired respiratory signal for inducing respiration of the patient;
a real respiration measurement step in which real respiration of the patient is measured and a real respiratory signal obtained through the measurement is outputted;
a respiration evaluation step in which by, as a calculation unit, utilizing data of a single period of the desired respiratory signal, there is calculated a pair of coefficients, of trigonometric functions, which correspond to the 1st-order terms by means of Fourier series expansion of the desired respiratory signal and the real respiratory signal, which is acquired in synchronization with the desired respiratory signal, and there are performed comparisons between the respective gains and between the respective phases, which are obtained from the calculated coefficients, so that there is evaluated a misalignment of the real respiration from the desired respiratory signal, and
a modification information generating step in which a modification information to modify the misalignment of the real respiration is generated, based on the evaluation results evaluated in the respiration evaluation step.

* * * * *